US012636090B2

(12) United States Patent
Massarwa et al.

(10) Patent No.: US 12,636,090 B2
(45) Date of Patent: May 26, 2026

(54) MAP DEFORMATION FOR ANATOMICAL MAPPING

(71) Applicant: Biosense Webster (Israel) Ltd.,
Yokneam (IL)

(72) Inventors: Fady Massarwa, Baka Al Gharbiyya
(IL); Ido Ilan, Yoqneam (IL)

(73) Assignee: **BIOSENSE WEBSTER (ISRAEL)
LTD.**, Yokneam (IL)

( * ) Notice: Subject to any disclaimer, the term of this
patent is extended or adjusted under 35
U.S.C. 154(b) by 0 days.

(21) Appl. No.: 18/512,580

(22) Filed: Nov. 17, 2023

(65) Prior Publication Data

US 2025/0160960 A1     May 22, 2025

(51) Int. Cl.
| *A61B 5/05* | (2021.01) |
| *A61B 18/14* | (2006.01) |
| *A61B 34/20* | (2016.01) |
| *G06T 7/20* | (2017.01) |
| *G16H 30/40* | (2018.01) |

(52) U.S. Cl.
CPC .......... *A61B 34/20* (2016.02); *A61B 18/1492*
(2013.01); *G06T 7/20* (2013.01); *G16H 30/40*
(2018.01); *A61B 2034/2055* (2016.02); *G06T*
*2219/2021* (2013.01)

(58) Field of Classification Search
CPC ................ A61B 34/20; A61B 18/1492; A61B
2034/2055; G16H 30/40
See application file for complete search history.

(56) References Cited

U.S. PATENT DOCUMENTS

| 5,391,199 A | 2/1995 | Ben-Haim |
| 5,443,489 A | 8/1995 | Ben-Haim |
| 5,558,091 A | 9/1996 | Acker et al. |
| 6,172,499 B1 | 1/2001 | Ashe |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,788,967 B2 | 9/2004 | Ben-Haim et al. |
| 6,892,091 B1 | 5/2005 | Ben-Haim et al. |
| 7,536,218 B2 | 5/2009 | Govari et al. |
| 7,610,078 B2 | 10/2009 | Willis |

(Continued)

FOREIGN PATENT DOCUMENTS

| WO | 2022207849 A1 | 10/2022 |
| WO | 2023126720 A1 | 7/2023 |

OTHER PUBLICATIONS

Extended European Search Report issued on May 19, 2025 for
European Patent Application No. 24213148.0.

*Primary Examiner* — Joel F Brutus

(74) *Attorney, Agent, or Firm* — Volpe Koenig

(57) ABSTRACT

A mapping engine is provided. The mapping engine operates
to generate on a display an initial visualization of an
anatomical structure during an ablation procedure and a
catheter at an average position as a silhouette below a
surface within the initial visualization. The mapping engine
operates to deform an area of the surface of the initial
visualization to the average position to generate a temporary
visualization exposing at least a portion of the catheter and
to determine whether to maintain the temporary visualiza-
tion based on an ablation event of the ablation procedure.

18 Claims, 23 Drawing Sheets

(56) References Cited

U.S. PATENT DOCUMENTS

| | | | |
|---|---|---|---|
| 7,756,576 B2 | 7/2010 | Levin | |
| 7,848,787 B2 | 12/2010 | Osadchy | |
| 7,869,865 B2 | 1/2011 | Govari et al. | |
| 8,456,182 B2 | 6/2013 | Bar-tal et al. | |
| 8,457,721 B2 | 6/2013 | Desai | |
| 8,784,414 B2 | 7/2014 | Avitall et al. | |
| 10,952,795 B2 | 3/2021 | Cohen et al. | |
| 2020/0286225 A1* | 9/2020 | Ben-Haim | G06T 19/00 |
| 2021/0241542 A1 | 8/2021 | Shmayahu et al. | |

* cited by examiner

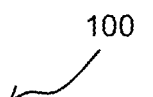
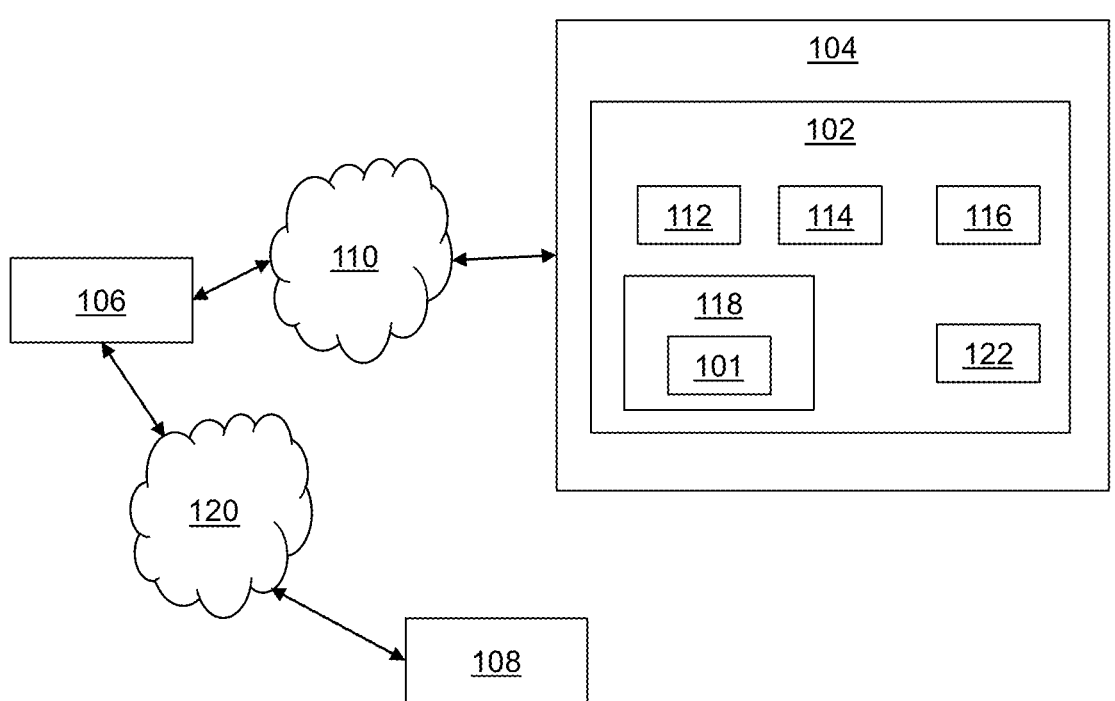
FIG. 2

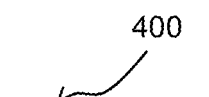
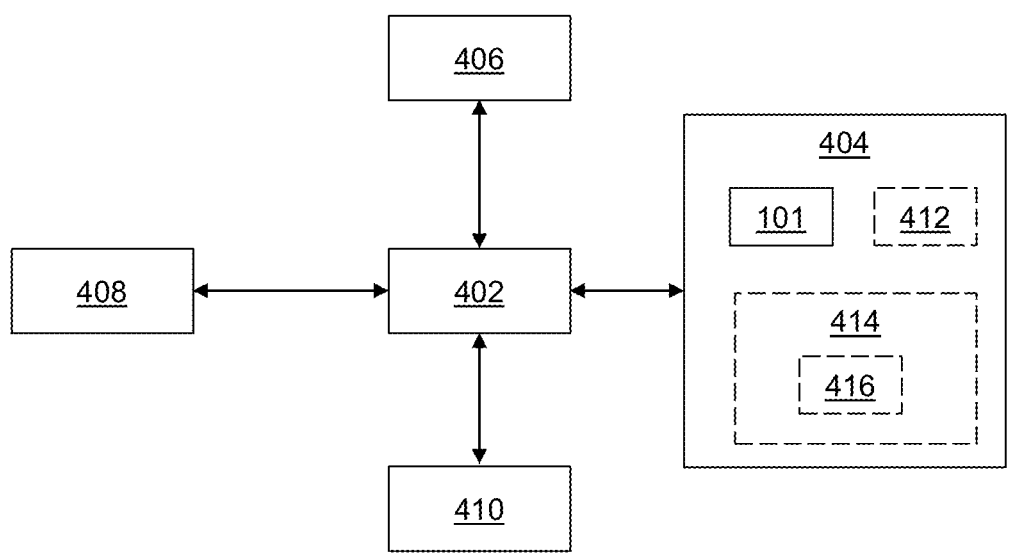
FIG. 4

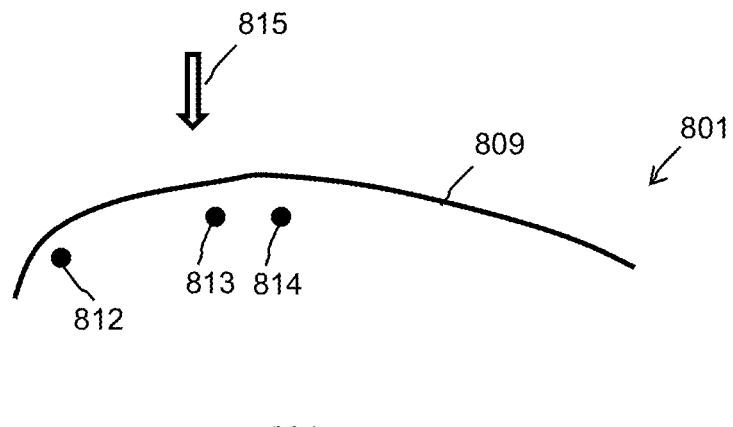
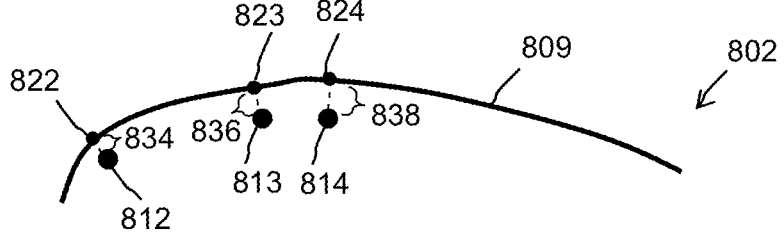
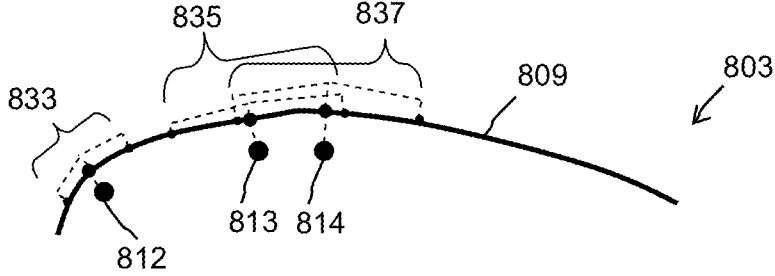
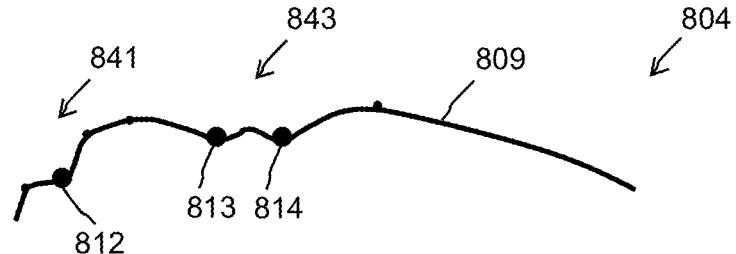
FIG. 8

1102

1111

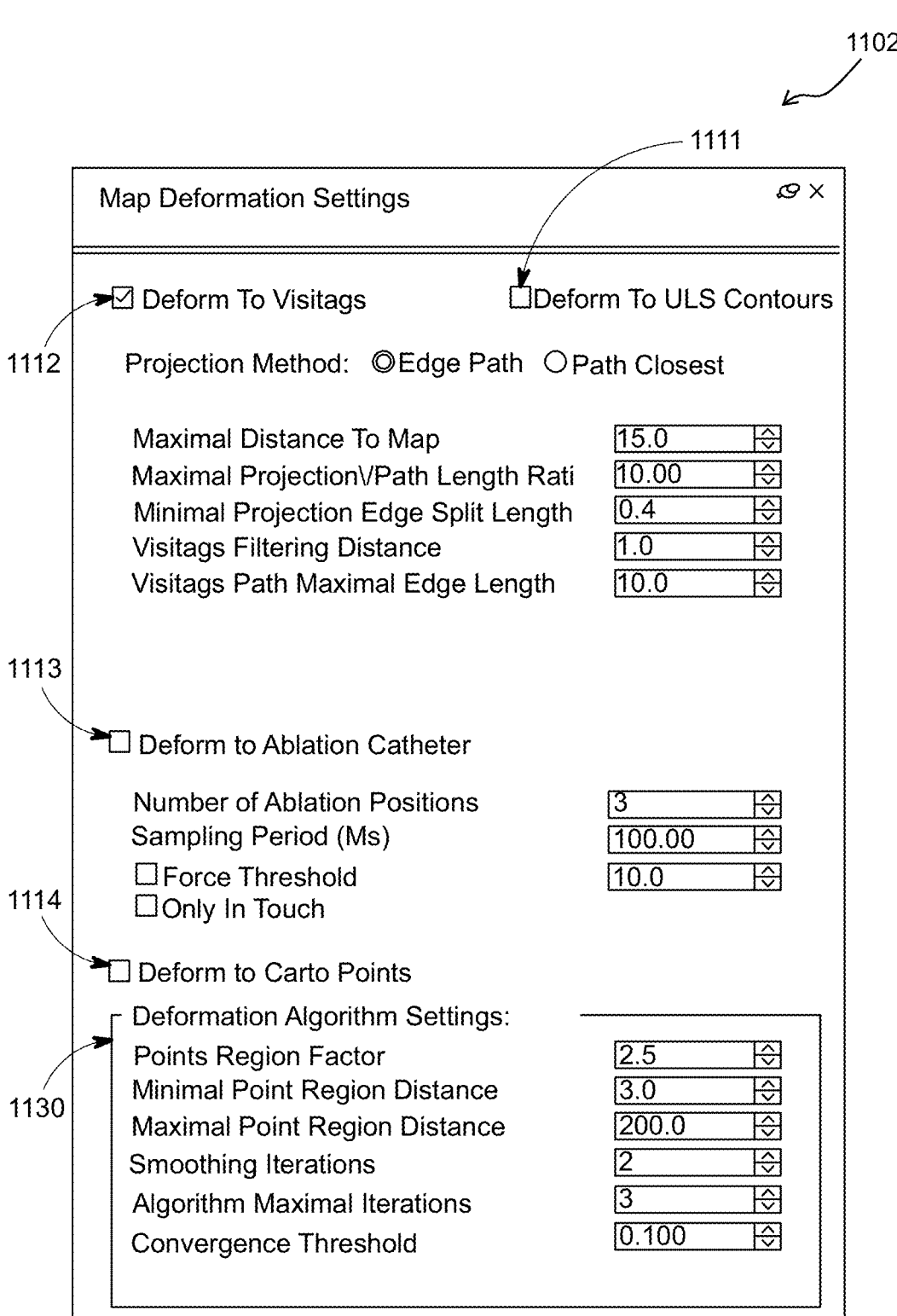

Map Deformation Settings                              ⟲ ✕

☑ Deform To Visitags          ☐ Deform To ULS Contours

1112

Projection Method:  ◉ Edge Path   ○ Path Closest

Maximal Distance To Map                    | 15.0 |
Maximal Projection\/Path Length Rati       | 10.00 |
Minimal Projection Edge Split Length       | 0.4 |
Visitags Filtering Distance                | 1.0 |
Visitags Path Maximal Edge Length          | 10.0 |

1113

☐ Deform to Ablation Catheter

Number of Ablation Positions               | 3 |
Sampling Period (Ms)                       | 100.00 |
☐ Force Threshold                          | 10.0 |
☐ Only In Touch

1114

☐ Deform to Carto Points

Deformation Algorithm Settings:

1130

Points Region Factor                       | 2.5 |
Minimal Point Region Distance              | 3.0 |
Maximal Point Region Distance              | 200.0 |
Smoothing Iterations                       | 2 |
Algorithm Maximal Iterations               | 3 |
Convergence Threshold                      | 0.100 |

FIG. 11

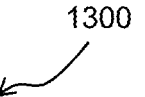
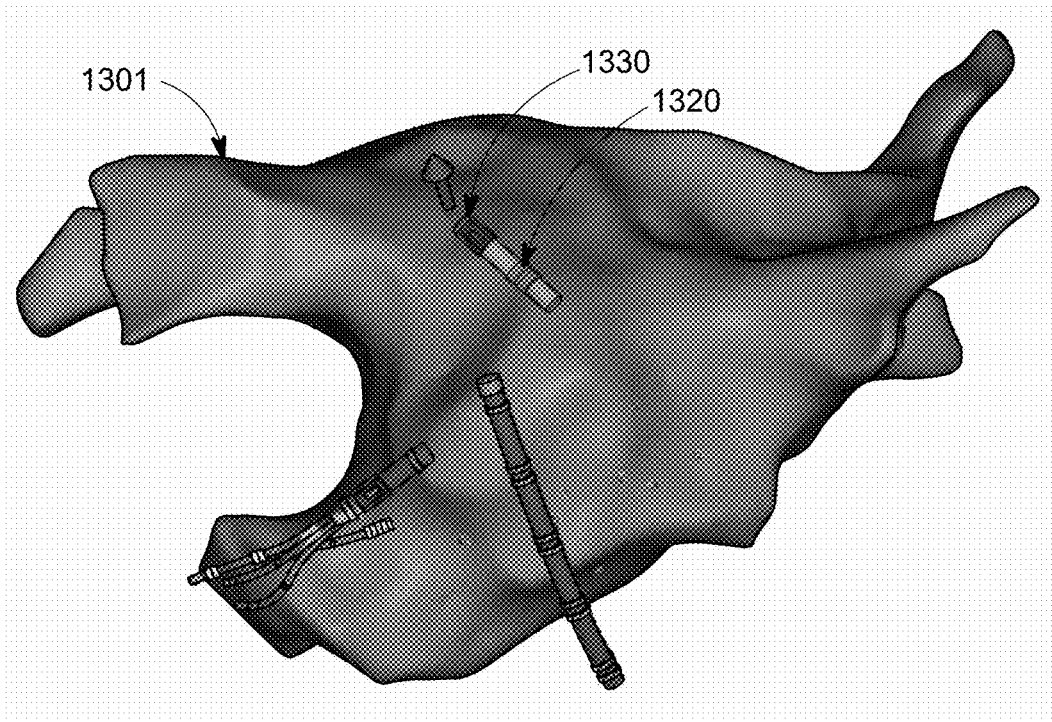
FIG. 13

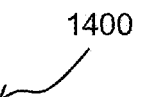
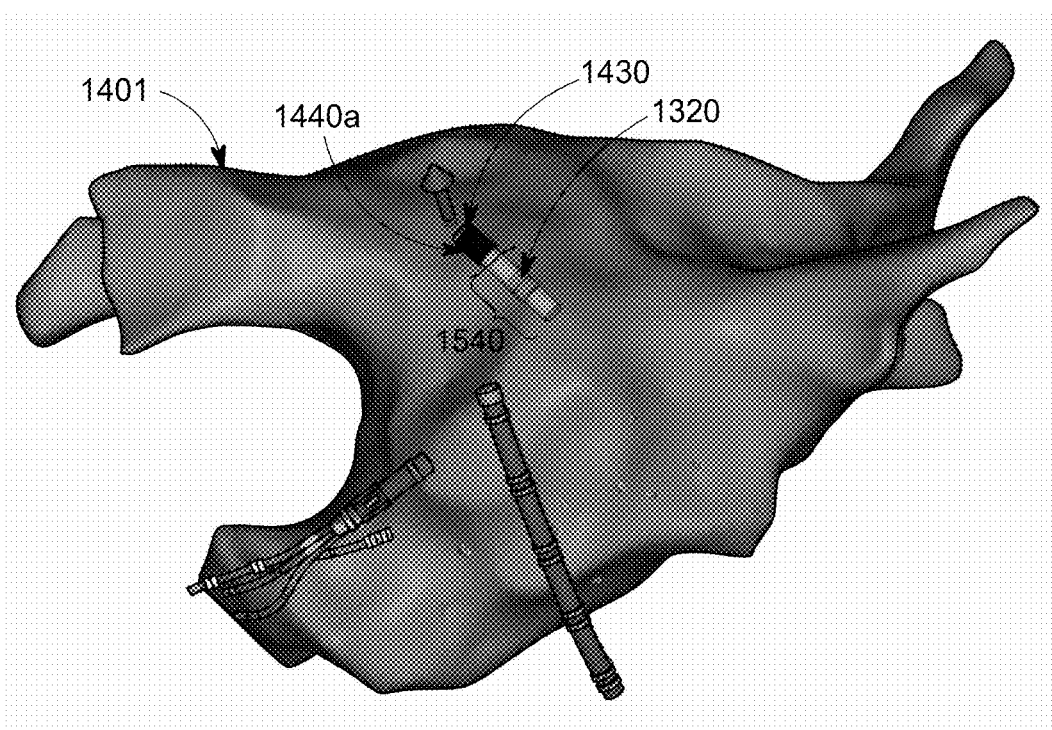
FIG. 14

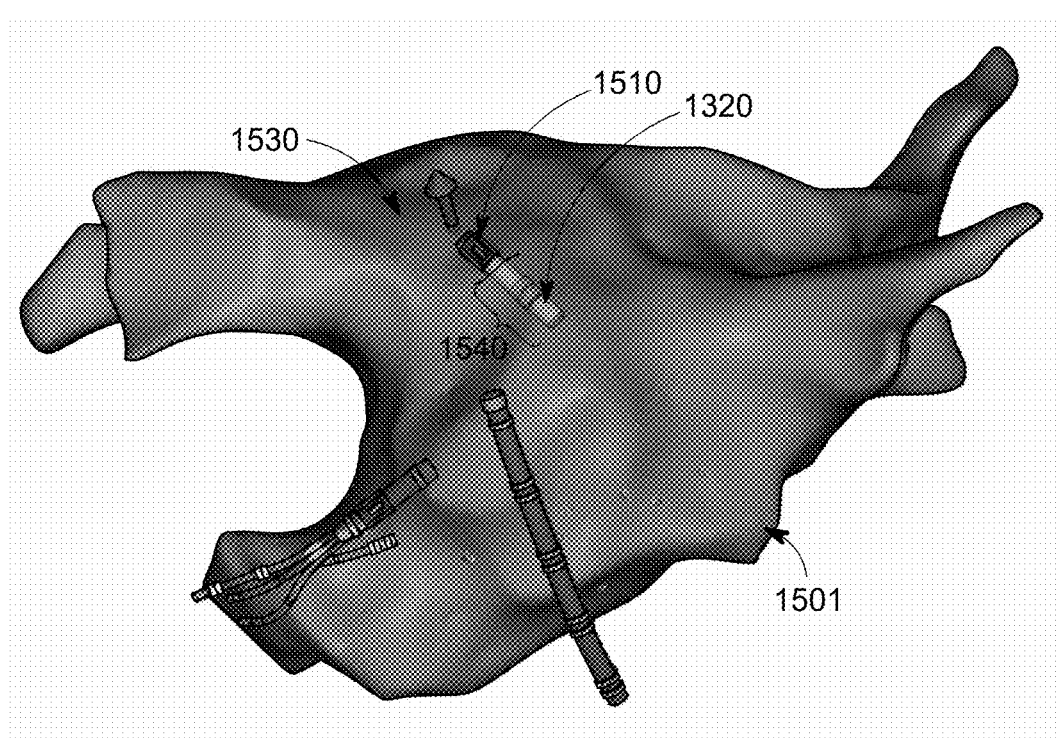
FIG. 15

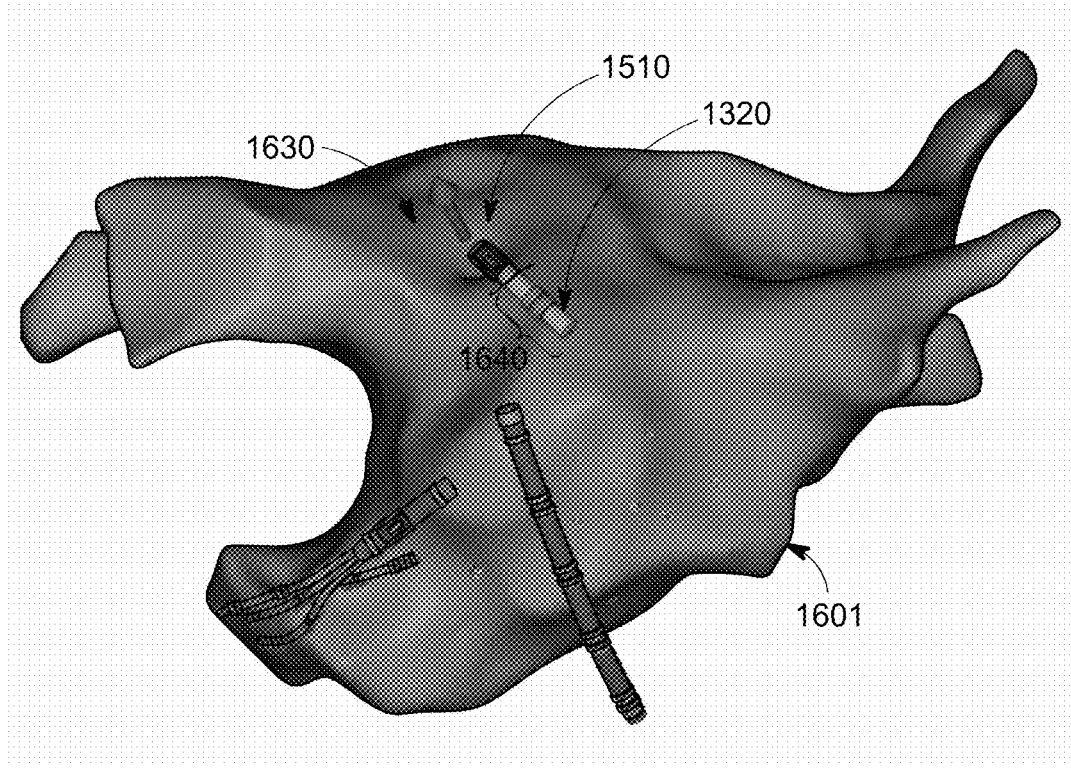
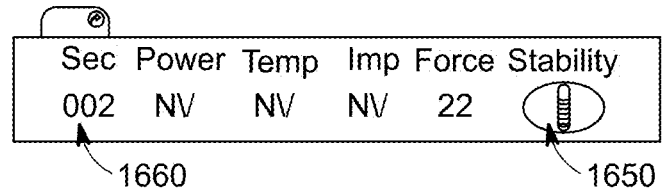
FIG. 16

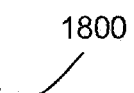
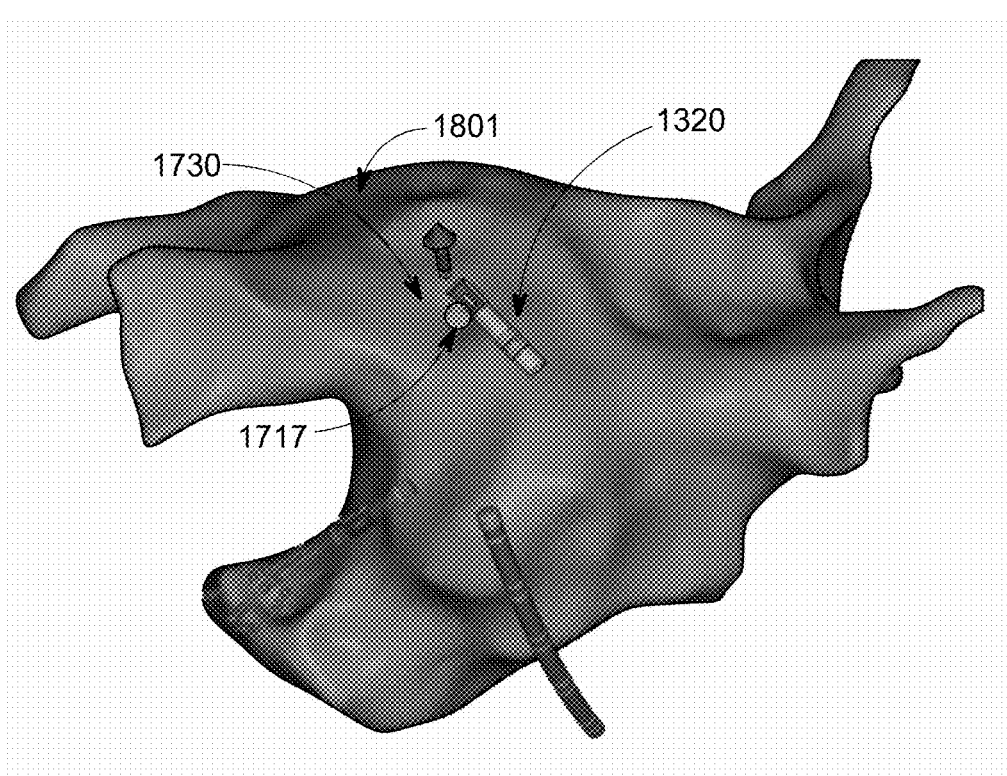
FIG. 18

MAP DEFORMATION FOR ANATOMICAL MAPPING

FIELD OF INVENTION

The present invention is related to anatomical mapping. More particularly, the present invention relates to map deformation for anatomical mapping.

BACKGROUND

Currently, catheter based radio frequency (RF) ablation for pulmonary vein isolation is a first line of treatment for atrial fibrillation (AF). RF ablation requires a very accurate map.

For example, during an electrophysiology (EP) procedure, an anatomical map of a heart chamber is generated. Fast anatomical mapping (FAM) is one algorithm for building such an anatomical map from electrical signals captured by a catheter on a myocardium. The anatomical map is used to guide a physician to desired ablation sites. As part of the building of the anatomical map (e.g., an aspect of generating the anatomical map of the FAM), a technician works sometimes may modify the volume of the FAM by performing a manual, time consuming process of shaving for a variety of reasons, including, e.g., to present a more anatomically accurate representation, to reveal annotations or anatomical points of interest that may have been obscured by the "shell" of the FAM. As part of the EP procedure, tags can be placed throughout the anatomical map in accordance with different action by the physician or operator. For instance, corresponding to each ablation event, a tag is placed at the ablation site within the anatomical map.

Generally, the anatomical map of the FAM can become oversized as the FAM continuously gathers volume (e.g., while the catheter moves and captures a largest size, for example when tissue is pushed). For instance, conventional mapping techniques capture an entire voxel when a threshold is matched. Additional factors for the FAM continuously gathering volume include continuous acquisition on all cardiac cycles, the patient's respiration, voxel size discretization, and tenting (e.g., pushing tissue with the catheter). As a result, a depiction of the catheter, the tags, and other features may not be visible on the anatomical map during the EP procedure.

Shaving is an act of removing voxels (from the volume). After the voxels are removed (shaved) the FAM surface is reconstructed again locally to reflect the shaving effect. The shaving modifies (removes part of) the input to the FAM reconstruction algorithm (which are the voxels). When used too extensively, shaving can lead to overshaving effects. For example, too much shaving on the input can lead to floating catheters and tags, misshaped maps, and removal of desired features.

Nonetheless, during the EP procedure, it can often be difficult for the physician to understand the relative positioning between the catheter and an ablation site (e.g., as annotated by the VISITAG®). In this regard, conventional mapping techniques can hide an ablation tip of the catheter (i.e., a depiction thereof), for example by a reconstruction during ablation, thereby hindering position determinations, distance estimations, and ablation decisions by the physician. Similarly, the physician can have difficulty understanding real tissue positioning (e.g., in real time and at a site by VISITAGS®).

A solution for a faster and more accurate mapping procedure that includes deformation of an output of the FAM to reveal the catheter, the tags, and other features that are hidden, provide more accurate positioning, and show the ablation tip is greatly needed.

SUMMARY

According to one or more embodiments, a mapping engine is provided. The mapping engine operates to generate on a display an initial visualization of an anatomical structure during an ablation procedure and a catheter at an average position as a silhouette below a surface within the initial visualization. The mapping engine operates to deform an area of the surface of the initial visualization to generate a temporary visualization, thereby exposing at least a portion of the catheter, and to determine whether to maintain the temporary visualization based on an ablation event of the ablation procedure.

According to one or more embodiments, a mapping engine is provided. The mapping engine operates to generate on a display an initial visualization of an anatomical structure comprising one or more tags hidden below a surface of the initial visualization and to deform an area of the surface to expose the one or more tags. The mapping engine operates to deform the area of the surface for each of the one or more tags by automatically selecting a surface point closest to a tag of the one or more tags, calculating a distance between the surface point and the tag, and determining the area of the surface to deform based on the distance. The mapping engine operates to generate a temporary visualization on the display based on the deforming of the area.

According to one or more embodiments, a mapping engine is provided. The mapping engine operates to generate on a display an initial visualization of an anatomical structure comprising one or more features hidden below a surface of the initial visualization and identify a subset of the one or more features according to a set of parameters. The mapping engine operates a deformation algorithm of the mapping engine to deform the surface of the initial visualization to expose the subset of the one or more features by changing one or more areas of the surface corresponding to the subset of the one or more tags.

According to one or more embodiments, the exemplary mapping engine embodiments above can be implemented as methods, apparatuses, systems, and/or computer program products.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 2 is a block diagram of an example system for remotely monitoring and communicating biometric data according to one or more embodiments;

FIG. 4 is a block diagram of an example device in which one or more features of the disclosure can be implemented according to one or more embodiments;

FIG. 8 depicts a set of illustrations providing an example deformation progression according to one or more embodiments;

FIG. 11 depicts a user interface according to one or more embodiments;

FIGS. 13-23 depict user interfaces presenting a progression of visualizations according to one or more embodiments.

DETAILED DESCRIPTION

Disclosed herein is a method and/or system for anatomical mapping. More particularly, the method and/or system relates to a mapping engine. The mapping engine is a processor executable code or software that is necessarily rooted in process operations by, and in processing hardware of, medical device equipment performing and using the anatomical mapping. The mapping engine implements the anatomical mapping to generate maps. The mapping engine can perform map deformation for the maps. For ease of explanation, the mapping engine is described herein with respect to mapping a heart. However, any anatomical structure, body part, organ, or portion thereof can be a target for mapping by the mapping engine described herein.

According to one or more embodiments, the mapping engine implements the anatomical mapping to generate maps of the heart that include an endocardial surface of a left atrium (LA). A map can be one three-dimensional (3D) model or a combination of multiple 3D models. The mapping engine can generate and edit the maps of the heart (e.g., provide real-time or post-processed map deformations or shape changes to the endocardial surface of the 3D model) in real time during an EP procedure (e.g., an ablation procedure). By way of example, the mapping engine can deform a surface of an initial visualization (e.g., an output of a FAM) to expose tags, a catheter, and/or points that are otherwise hidden, thereby improving the operations and outcomes of the anatomical mapping. Accordingly, the mapping engine improves conventional mapping techniques by reducing clutter across the maps and providing clear and accurate depictions of the tags, the catheter, and/or points of the catheter within the maps. Further, one or more advantages, technical effects, and/or benefits of the mapping engine can include providing a mechanism to understand a relative position between the catheter and ablation sites that is otherwise not available due to the limitations of conventional techniques.

Figure 1:
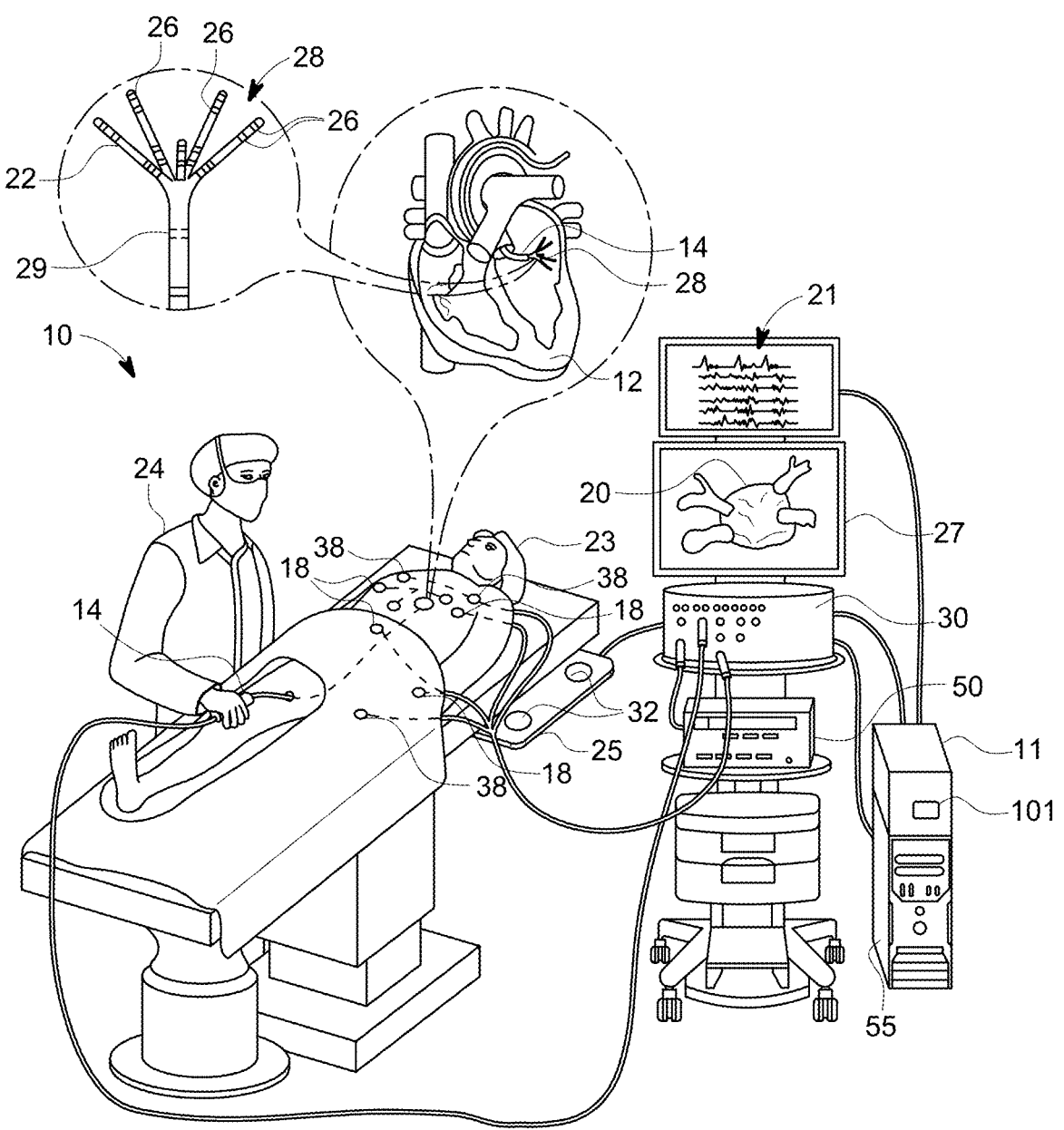
FIG. 1 depicts an example catheter-based electrophysiology mapping and ablation system according to one or more embodiments.

Reference is made to FIG. 1 showing an example system (e.g., medical device equipment and/or catheter-based electrophysiology mapping and ablation system), shown as system 10, in which one or more features of the subject matter herein can be implemented according to one or more embodiments. All or part of the system 100 can be used to collect information (e.g., biometric data) and/or used to implement a (e.g., a mapping engine 101) as described herein. In some examples, the mapping engine 101 is implemented using a processor executable code or software that is stored on a memory of the system 10 and that is necessarily rooted in process operations by, and in processing hardware of, the system 10. As described herein, the mapping engine 101 can generate maps (a.k.a. visualizations) and provide map deformations or shape changes to the maps.

FIG. 1 illustrates a recorder 11, a heart 12, a catheter 14, a model or anatomical map 20, an electrogram 21, a spline 22, a patient 23, a physician 24 (which is representative of any medical professional, technician, clinician, operator, clinical support specialist, clinical account specialist, healthcare personnel, etc.), a location pad 25, one or more electrodes 26, a display device 27, a distal tip 28, a sensor 29, a coil 32, a patient interface unit (PIU) 30, electrode skin patches 38, an ablation energy generator 50, and a workstation 55. Note further each element and/or item of the system 10 is representative of one or more of that element and/or that item. The example system 10 shown in FIG. 1 implements the embodiments disclosed herein. The disclosed embodiments can similarly be applied using other system components and settings. Additionally, the system 10 can include additional components, for example elements for sensing electrical activity, wired or wireless connectors, processing and display devices, or other components.

The system 10 includes multiple catheters 14, which are percutaneously inserted by the physician 24 through the patient's vascular system into a chamber or vascular structure of the heart 12. Typically, a delivery sheath catheter is inserted into the left or right atrium near a desired location in the heart 12. Thereafter, a plurality of catheters can be inserted into the delivery sheath catheter to arrive at the desired location. The plurality of catheters 14 may include catheters dedicated for sensing Intracardiac Electrogram (IEGM) signals, catheters dedicated for ablating, and/or catheters dedicated for both sensing and ablating. The example catheter 14 that is configured for sensing IEGM is illustrated herein. The physician 24 brings the distal tip 28 of the catheter 14 into contact with a heart wall for sensing a target site in the heart 12. For ablation, the physician 24 would similarly bring a distal end of an ablation catheter to a target site for ablating.

The catheter 14 is an exemplary catheter that includes at least one and preferably multiple electrodes 26 optionally distributed over a plurality of splines 22 at the distal tip 28 and configured to sense the IEGM signals. The catheter 14 may additionally include the sensor 29 embedded in or near the distal tip 28 for tracking position and orientation of the distal tip 28. Optionally and preferably, the position sensor 29 is a magnetic based position sensor including three magnetic coils for sensing 3D position and orientation. According to one or more embodiments, shape and parameters of the catheter 14 vary based on whether the catheter 14 is used for diagnostic or ablation purposes, the type of arrhythmia, patient anatomy, and other factors, which affects catheter maneuverability (e.g., an ability to touch without bending the surface and the tracked parts of the catheter 14). The shape and parameters of the catheter 14 also impact the accuracy of anatomical maps. Large spherical single-shot catheters, which can ablate a pulmonary vein within seconds, have become popular but require guidance from fluoroscopy, CT/MRI, or additional mapping catheters. The operations of the mapping engine 101 resolve the shortcomings of the catheter 14, by performing map deformation to reveal items of interest, such as the catheter 14 during an EP procedure, or tags that may otherwise be hidden, as described herein.

The sensor 29 (e.g., a position or a magnetic based position sensor) may be operated together with the location pad 25 including a plurality of magnetic coils 32 configured to generate magnetic fields in a predefined working volume. Real time position of the distal tip 28 of the catheter 14 may be tracked based on magnetic fields generated with the location pad 25 and sensed by the sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

The system 10 includes one or more electrode patches 38 positioned for skin contact on the patient 23 to establish location reference for the location pad 25 as well as impedance-based tracking of the electrodes 26. For impedance-based tracking, electrical current is directed toward the electrodes 26 and sensed at the patches 38 (e.g., electrode skin patches) so that the location of each electrode can be triangulated via the patches 38. Details of the impedance-based location tracking technology are described in U.S. Pat. Nos. 7,536,218; 7,756,576; 7,848,787; 7,869,865; and 8,456,182, which are incorporated herein by reference.

The recorder 11 displays the electrograms 21 captured with the electrodes 18 (e.g., body surface electrocardiogram (ECG) electrodes) and intracardiac electrograms (IEGM) captured with the electrodes 26 of the catheter 14. The recorder 11 may include pacing capability for pacing the heart rhythm and/or may be electrically connected to a standalone pacer.

The system 10 may include the ablation energy generator 50 that is adapted to conduct ablative energy to the one or more of electrodes 26 at the distal tip 28 of the catheter 14 configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

The PIU 30 is an interface configured to establish electrical communication between catheters, electrophysiological equipment, power supply and the workstation 55 for controlling operation of the system 10. Electrophysiological equipment of the system 10 may include for example, multiple catheters 14, the location pad 25, the body surface ECG electrodes 18, the electrode patches 38, the ablation energy generator 50, and the recorder 11. Optionally and preferably, the PIU 30 additionally includes processing capability for implementing real-time computations of location of the catheters and for performing ECG calculations.

The workstation 55 includes memory, a processor unit with memory or storage with appropriate operating software loaded therein, and user interface capability (e.g., the memory or storage of the workstation 55 stores the mapping engine 101 and the processor unit of the workstation 55 executes the mapping engine 101). The workstation 55, for example by utilizing the mapping engine 101, may provide multiple functions, optionally including modeling the endocardial anatomy in three-dimensions (3D) and rendering the model or anatomical map 20 (e.g., a visualization) for display on the display device 27, displaying on the display device 27 activation sequences (or other data) compiled from recorded electrograms 21 in representative visual indicia or imagery superimposed on the rendered anatomical map 20, displaying real-time location and orientation of multiple catheters within the heart chamber, and displaying on the display device 27 sites of interest for example places where ablation energy has been applied. One commercial product embodying elements of the system 10 is available as the CARTO™ 3 System, available from Biosense Webster, Inc., 31A Technology Drive, Irvine, CA 92618. Note that modeling the endocardial anatomy in 3D can include generating a surface thereof as a triangular mesh.

For instance, the system 10 can be part of a surgical system (e.g., CARTO® system sold by Biosense Webster) that is configured to obtain biometric data (e.g., anatomical and electrical measurements of a patient's organ, for example the heart 12 and as described herein) and perform a cardiac ablation procedure. More particularly, treatments for cardiac conditions for example cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in a chamber of the heart 12. Such locating may be done via an electrophysiological investigation during which electrical potentials are detected and spatially resolved with a mapping catheter (e.g., the catheter 14) introduced into the chamber of the heart 12. This electrophysiological investigation, the so-called electro-anatomical mapping (as described herein according to one or more embodiments of the mapping engine 101), thus provides 3D mapping data which can be displayed on the display device 27. In many cases, the mapping function (e.g., by the mapping engine 101) and a treatment function (e.g., ablation) are provided by a single catheter or group of catheters such that the mapping catheter also operates as a treatment catheter at the same time.

FIG. 2 is a block diagram of an example system 100 for remotely monitoring and communicating biometric data (e.g., patient biometrics). In the example illustrated in FIG. 2, the system 100 includes a patient biometric monitoring and processing apparatus 102 associated with a patient 104, a local computing device 106, a remote computing system 108, a first network 110, a patient biometric sensor 112, a processor 114, a user input (UI) sensor 116, a memory 118, a second network 120, and a transmitter-receiver (i.e., transceiver) 122.

According to one or more embodiments, the patient biometric monitoring and processing apparatus 102 may be an apparatus that is internal to the patient's body (e.g., subcutaneously implantable), for example the catheter 14 of FIG. 1. The patient biometric monitoring and processing apparatus 102 may be inserted into a patient via any applicable manner including orally injecting, surgical insertion via a vein or artery, an endoscopic procedure, or a laparoscopic procedure.

According to one or more embodiments, the patient biometric monitoring and processing apparatus 102 may be an apparatus that is external to the patient, for example the electrode patches 38 of FIG. 1. For example, as described in more detail below, the patient biometric monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to one or more embodiments, the patient biometric monitoring and processing apparatus 102 may include both components that are internal to the patient and components that are external to the patient.

A single patient biometric monitoring and processing apparatus 102 is shown in FIG. 2. Example systems may, however, may include a plurality of patient biometric monitoring and processing apparatuses. A patient biometric monitoring and processing apparatus may be in communication with one or more other patient biometric monitoring and processing apparatuses. Additionally or alternatively, a patient biometric monitoring and processing apparatus may be in communication with the network 110.

One or more patient biometric monitoring and processing apparatuses 102 may acquire biometric data (e.g., patient biometrics, for example electrical signals, blood pressure, temperature, blood glucose level, or other biometric data) and receive at least a portion of the biometric data representing the acquired patient biometrics and additional information associated with the acquired patient biometrics from one or more other patient biometric monitoring and processing apparatuses 102. The additional information may be, for example, diagnosis information and/or additional information obtained from an additional device, for example a wearable device. Each of the patient biometric monitoring and processing apparatus 102 may process data, including its own biometric data as well as data received from one or more other patient biometric monitoring and processing apparatuses 102.

Biometric data (e.g., patient biometrics, patient data, or patient biometric data) can include one or more of local activation times (LATs), electrical activity, topology, bipolar mapping, reference activity, ventricle activity, dominant frequency, impedance, or other data. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, intracardiac electrocardiogram (IC ECG) data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treat any number of various diseases, for example cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

In FIG. 2, the network 110 is an example of a short-range network (e.g., local area network (LAN), or personal area network (PAN)). Information may be sent, via the network 110, between the patient biometric monitoring and processing apparatus 102 and the local computing device 106 using any one of various short-range wireless communication protocols, for example Bluetooth, Wi-Fi, Zigbee, Z-Wave, near field communications (NFC), ultraband, Zigbee, or infrared (IR).

The network 120 may be a wired network, a wireless network or include one or more wired and wireless networks. For example, the network 120 may be a long-range network (e.g., wide area network (WAN), the internet, or a cellular network). Information may be sent, via the network 120 using any one of various long-range wireless communication protocols (e.g., TCP/IP, HTTP, 3G, 4G/LTE, or 5G/New Radio).

The patient biometric monitoring and processing apparatus 102 may include the patient biometric sensor 112, the processor 114, the UI sensor 116, the memory 118, and the transceiver 122. The patient biometric monitoring and processing apparatus 102 may continually or periodically monitor, store, process and communicate, via the network 110, any number of various biometric data. Examples of biometric data include electrical signals (e.g., ECG signals and brain biometrics), blood pressure data, blood glucose data, and temperature data. The biometric data may be monitored and communicated for treatment across any number of various diseases, for example cardiovascular diseases (e.g., arrhythmias, cardiomyopathy, and coronary artery disease) and autoimmune diseases (e.g., type I and type II diabetes).

The patient biometric sensor 112 may include, for example, one or more sensors configured to sense a type of biometric data. For example, the patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

As described in more detail below, the patient biometric monitoring and processing apparatus 102 may be an ECG monitor for monitoring ECG signals of a heart (e.g., the heart 12). The patient biometric sensor 112 of the ECG monitor may include one or more electrodes for acquiring ECG signals. The ECG signals may be used for treatment of various cardiovascular diseases, as well as anatomical mapping.

The transceiver 122 may include a separate transmitter and receiver. Alternatively, the transceiver 122 may include a transmitter and receiver integrated into a single device.

The processor 114 may be configured to store biometric data in the memory 118 acquired by the patient biometric sensor 112 and to communicate the biometric data across the network 110 via a transmitter of the transceiver 122. Data from one or more other patient biometric monitoring and processing apparatus 102 may also be received by a receiver of the transceiver 122, as described in more detail herein. By way of example, the mapping engine 101 of FIG. 1 is a processor executable code or software that can be stored on the memory 118 (as shown) and executed by the processor 114. By way of further example, the mapping engine 101 can also be stored and executed on the local computing device 106 and/or the remote computing system 108. Thus, the mapping engine 101 that is necessarily rooted in process operations by, and in processing hardware of, the system 100.

According to one or more embodiments, the mapping engine 101 operates to generate on a display (e.g., display device 27) an initial visualization of an anatomical structure during an ablation procedure and a catheter (e.g., the catheter 14) at an average position as a silhouette below a surface within the initial visualization (e.g., stitched under the surface). The mapping engine 101 operates to deform an area of the surface of the initial visualization to the average position to generate a temporary visualization exposing at least a portion of the catheter and to determine whether to maintain the temporary visualization based on an ablation event of the ablation procedure.

According to one or more embodiments, the mapping engine 101 operates to generate on a display (e.g., display device 27) an initial visualization of an anatomical structure comprising one or more tags hidden below a surface of the initial visualization and to deform an area of the surface to expose the one or more tags. The mapping engine 101 operates to deform the area of the surface for each of the one or more tags by automatically selecting a surface point closest to a tag of the one or more tags, calculating a distance between the surface point and the tag, and determining the area of the surface to deform based on the distance. The mapping engine 101 operates to generate a temporary visualization on the display based on the deforming of the area.

According to one or more embodiments, the mapping engine 101 operates to generate on a display an initial visualization of an anatomical structure comprising one or more features hidden below a surface of the initial visualization and identify a subset of the one or more features according to a set of parameters The mapping engine 101 operates a deformation algorithm of the mapping engine 101 to deform the surface of the initial visualization to expose the subset of the one or more features by changing one or more areas of the surface corresponding to the subset of the one or more tags.

According to one or more embodiments, the patient biometric monitoring and processing apparatus 102 includes UI sensor 116 that may be, for example, a piezoelectric sensor or a capacitive sensor configured to receive a user input, for example a tapping or touching. For example, the UI sensor 116 may be controlled to implement a capacitive coupling, in response to tapping or touching a surface of the patient biometric monitoring and processing apparatus 102 by the patient 104. Gesture recognition may be implemented via any one of various capacitive types, for example resistive capacitive, surface capacitive, projected capacitive, surface acoustic wave, piezoelectric and infra-red touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from the patient biometric monitoring and processing apparatus 102 when a gesture is detected.

The local computing device 106 of the system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via the network 120. Alternatively, the local computing device 106 may be a stationary or standalone device, for example a stationary base station including, for example, modem and/or router capability, a desktop or laptop computer using an executable program to communicate information between the patient biometric monitoring and processing apparatus 102 and the remote computing system 108 via the PC's radio module, or a USB dongle. Biometric data may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, for example a local area network (LAN) (e.g., a personal area network (PAN)). In some embodiments, the local computing device 106 may also be configured to display the acquired patient electrical signals and information associated with the acquired patient electrical signals, as described in more detail herein.

In some embodiments, the remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, for example any of the wireless technologies mentioned above. As described in more detail below, the remote computing system 108 may be configured to provide (e.g., visually display and/or aurally provide) the at least one of the patient biometrics and the associated information to the physician 24.

Figure 3:
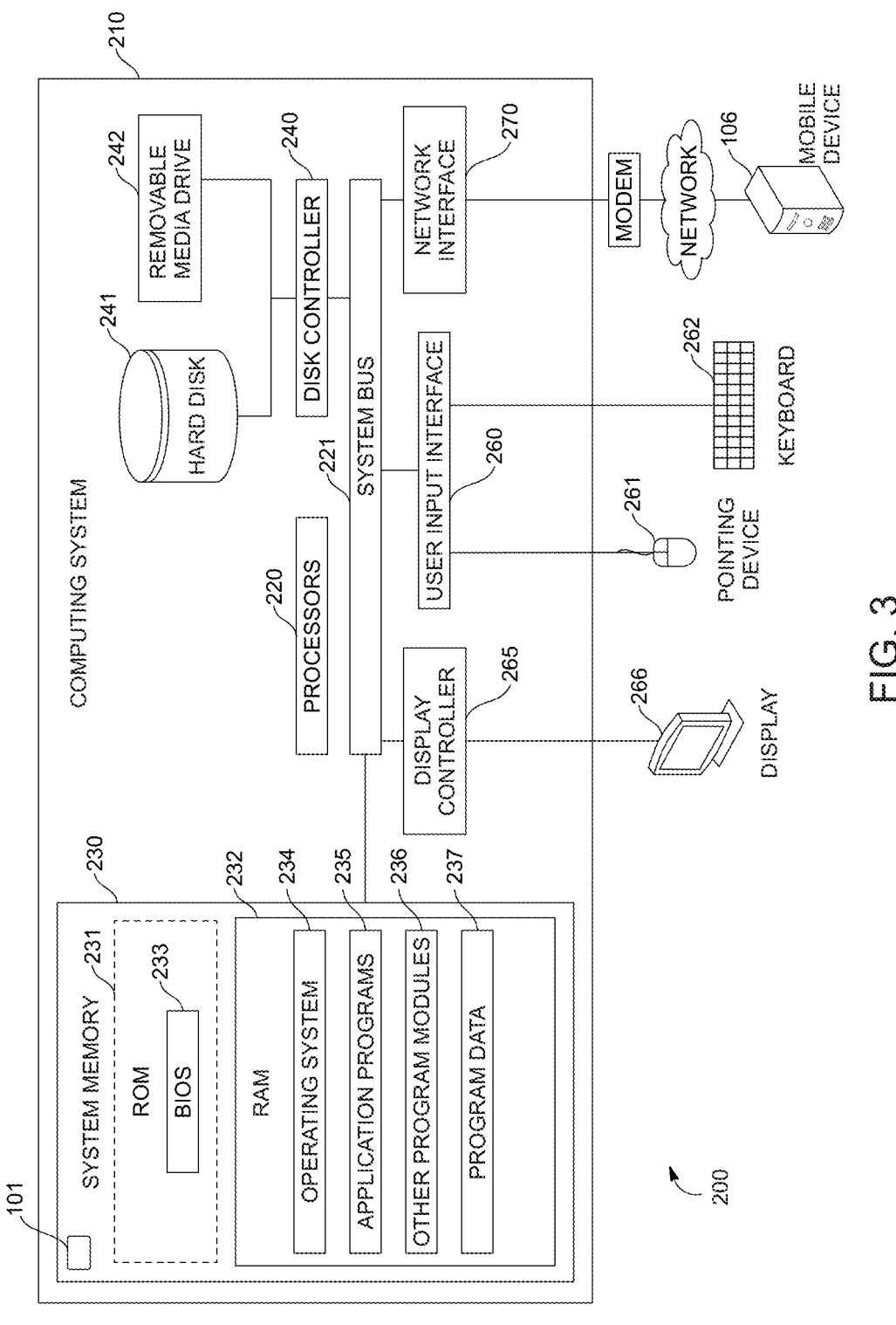
FIG. 3 is a system diagram of an example computing environment in communication with a network according to one or more embodiments.

FIG. 3 is a system diagram of an example of a computing environment 200 in communication with network 120. In some instances, the computing environment 200 is incorporated in a public cloud computing platform (e.g., Amazon Web Services or Microsoft Azure), a hybrid cloud computing platform (e.g., HP Enterprise OneSphere) or a private cloud computing platform.

As shown in FIG. 3, computing environment 200 includes a computer system 210, which is one example of the workstation 55 of FIG. 1, the local computing device 106 of FIG. 2, and/or the remote computing system 108 of FIG. 2 upon which embodiments described herein may be implemented. By way of example, the mapping engine 101 of FIG. 1 is a processor executable code or software that can be stored on the system memory 231 (as shown) and executed by processors 220, such that the mapping engine 101 that is necessarily rooted in process operations by, and in processing hardware of, the computing environment 200.

The computer system 210 may, via processors 220, which may include one or more processors, perform various functions. The functions may include analyzing monitored biometric data and the associated information and, according to physician-determined or algorithm driven thresholds and parameters, providing (e.g., via display 266) alerts, additional information or instructions. The functions may include the operation of the mapping engine 101, for example to perform map deformation for anatomical mapping as described herein. As described in more detail herein, the computer system 210 may be used to provide (e.g., via display 266) the physician 24 of FIG. 1 with a dashboard of patient information, such that such information may enable the physician 24 to identify and prioritize patients having more critical needs than others.

As shown in FIG. 3, the computer system 210 may include a communication mechanism, for example a bus 221 or other communication mechanism for communicating information within the computer system 210. The computer system 210 further includes one or more processors 220 coupled with the bus 221 for processing the information. The processors 220 may include one or more CPUs, GPUs, or any other processor known in the art.

The computer system 210 also includes a system memory 230 coupled to the bus 221 for storing information and instructions to be executed by processors 220. The system memory 230 may include computer readable storage media in the form of volatile and/or nonvolatile memory, for example read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device(s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within computer system 210, for example during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

The illustrated computer system 210 also includes a disk controller 240 coupled to the bus 221 to control one or more storage devices for storing information and instructions, for example a magnetic hard disk 241 and a removable media drive 242 (e.g., floppy disk drive, compact disc drive, tape drive, and/or solid state drive). The storage devices may be added to the computer system 210 using an appropriate device interface (e.g., a small computer system interface (SCSI), integrated device electronics (IDE), Universal Serial Bus (USB), or FireWire).

The computer system 210 may also include a display controller 265 coupled to the bus 221 to control a monitor or display 266, for example a cathode ray tube (CRT) or liquid crystal display (LCD), for displaying information to a computer user. The illustrated computer system 210 includes a user input interface 260 and one or more input devices, for example a keyboard 262 and a pointing device 261, for interacting with a computer user and providing information to the processor 220. The pointing device 261, for example, may be a mouse, a trackball, or a pointing stick for communicating direction information and command selections to the processor 220 and for controlling cursor movement on the display 266. The display 266 may provide a touch screen interface that may allow input to supplement or replace the communication of direction information and command selections by the pointing device 261 and/or keyboard 262.

The computer system 210 may perform a portion or each of the functions and methods described herein in response to the processors 220 executing one or more sequences of one or more instructions contained in a memory, for example, the system memory 230. Such instructions may be read into the system memory 230 from another computer readable medium, for example, a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the computer system 210 may include at least one computer readable medium or memory for holding instructions programmed according to embodiments described herein (e.g., embodiments of the mapping engine 101) and for containing data structures, tables, records, or other data described herein. The term computer readable medium as used herein refers to any non-transitory, tangible medium that participates in providing instructions to the processor 220 for execution. A computer readable medium may take many forms including, but not limited to, non-volatile media, volatile media, and transmission media. Non-limiting examples of non-volatile media include optical disks, solid state drives, magnetic disks, and magneto-optical disks, for example hard disk 241 or removable media drive 242. Non-limiting examples of volatile media include dynamic memory, for example system memory 230. Non-limiting examples of transmission media include coaxial cables, copper wire, and fiber optics, including the wires that make up the bus 221. Transmission media may also take the form of acoustic or light waves, for example those generated during radio wave and infrared data communications.

The computing environment 200 may further include the computer system 210 operating in a networked environment using logical connections to local computing device 106 and one or more other devices, for example a personal computer (laptop or desktop), mobile devices (e.g., patient mobile devices), a server, a router, a network PC, a peer device or other common network node, and typically includes many or all of the elements described above relative to computer system 210. When used in a networking environment, computer system 210 may include modem 272 for establishing communications over a network 120, for example the Internet. Modem 272 may be connected to system bus 221 via network interface 270, or via another appropriate mechanism.

Network 120, as shown in FIGS. 2 and 3, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 210 and other computers (e.g., local computing device 106).

FIG. 4 is a block diagram of an example device 400 in which one or more features of the disclosure can be implemented. The device 400 may be local computing device 106, for example. The device 400 can include, for example, a computer, a gaming device, a handheld device, a set-top box, a television, a mobile phone, or a tablet computer. The device 400 includes a processor 402, a memory 404, a storage device 406, one or more input devices 408, and one or more output devices 410. The device 400 can also optionally include an input driver 412 and an output driver 414. It is understood that the device 400 can include additional components not shown in FIG. 4 including an artificial intelligence accelerator.

In various alternatives, the processor 402 includes a central processing unit (CPU), a graphics processing unit (GPU), a CPU and GPU located on the same die, or one or more processor cores, wherein each processor core can be a CPU or a GPU. In various alternatives, the memory 404 is located on the same die as the processor 402, or is located separately from the processor 402. The memory 404 includes a volatile or non-volatile memory, for example, random access memory (RAM), dynamic RAM, or a cache. By way of example, the mapping engine 101 of FIG. 1 is a processor executable code or software that can be stored on the memory 404 (as shown) and executed by processor 402, such that the mapping engine 101 that is necessarily rooted in process operations by, and in processing hardware of, the example device 400.

The storage device 406 includes a fixed or removable storage means, for example, a hard disk drive, a solid state drive, an optical disk, or a flash drive. The input devices 408 include, without limitation, a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The output devices 410 include, without limitation, a display device, a speaker, a printer, a haptic feedback device, one or more lights, an antenna, or a network connection (e.g., a wireless local area network card for transmission and/or reception of wireless IEEE 802 signals).

The input driver 412 communicates with the processor 402 and the input devices 408, and permits the processor 402 to receive input from the input devices 408. The output driver 414 communicates with the processor 402 and the output devices 410, and permits the processor 402 to send output to the output devices 410. It is noted that the input driver 412 and the output driver 414 are optional components, and that the device 400 will operate in the same manner if the input driver 412 and the output driver 414 are not present. The output driver 414 includes an accelerated processing device ("APD") 416 which communicates to a display device as represented by the output devices 410. The APD 416 accepts compute commands and graphics rendering commands from processor 402, processes those compute and graphics rendering commands, and provides pixel output to display device for display. As described in further detail below, the APD 416 includes one or more parallel processing units to perform computations in accordance with a single-instruction-multiple-data ("SIMD") paradigm. Thus, although various functionality is described herein as being performed by or in conjunction with the APD 416, in various alternatives, the functionality described as being performed by the APD 416 is additionally or alternatively performed by other computing devices having similar capabilities that are not driven by a host processor (e.g., processor 402) and provides graphical output to a display device. For example, it is contemplated that any processing system that performs processing tasks in accordance with a SIMD paradigm may perform the functionality described herein. Alternatively, it is contemplated that computing systems that do not perform processing tasks in accordance with a SIMD paradigm perform the functionality described herein.

Figure 5:
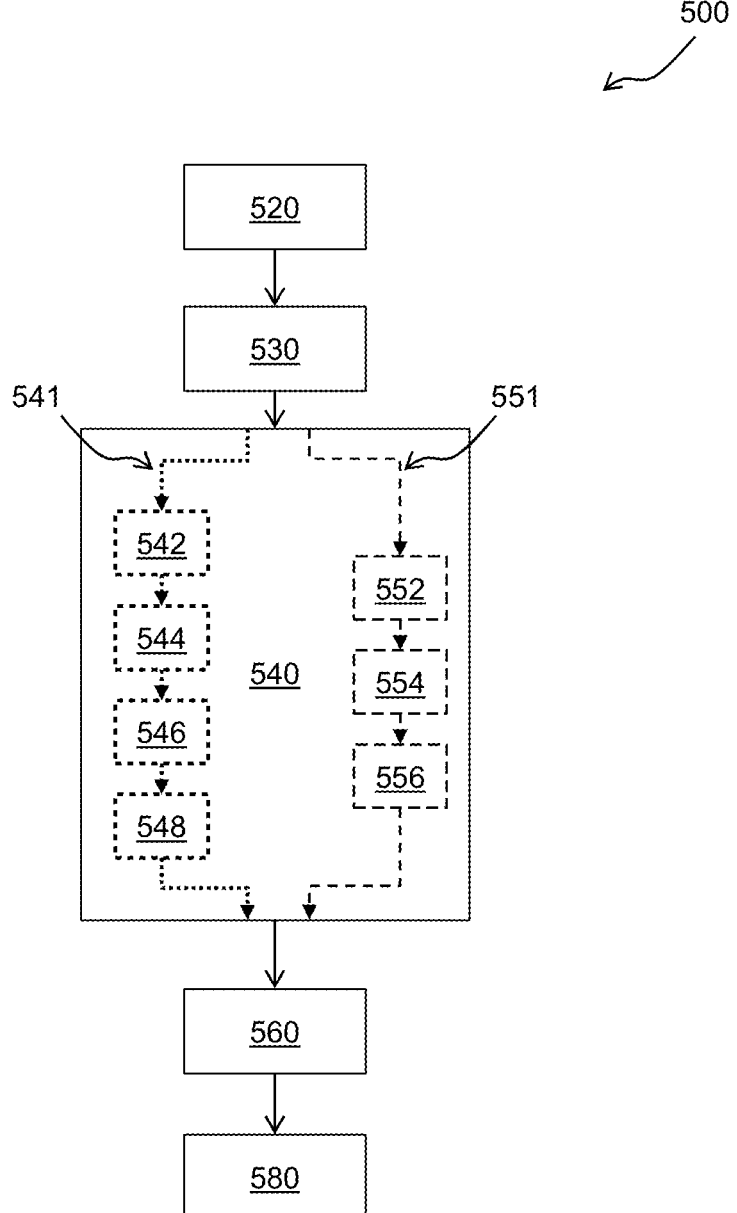
FIG. 5 depicts a method according to one or more embodiments.

Turning now to FIG. 5, a method 500 is illustrated according to one or more exemplary embodiments. The method 500 is an example set of operations by the mapping engine 101 being necessarily rooted in and executed by the workstation 55 of FIG. 1, the local computing device 106 of FIG. 2, the remote computing system 108 of FIG. 2, and/or the example device 400 of FIG. 4. The method 500 shows an example of how the mapping engine 101 generates and presents maps of an anatomical structure (e.g., one or more 3D models) and edits the maps (e.g., provides map deformation one or more 3D models), for example during an EP procedure (e.g., an ablation procedure).

The method 500 begins at block 520, where the mapping engine 101 generates an initial visualization. Part of generating the initial visualization includes presenting the initial visualization by a display as described herein.

The initial visualization is a map of an anatomical structure. For example, the initial visualization can be a 3D rendering of a heart chamber and include a rendering of the catheter within the heart chamber (in an actual position). The initial visualization can be considered a preview of or initial look at the heart chamber that guides the physician 24 to desired ablation sites with ease of understanding real tissue positioning. Note that dimensional understanding is extremely difficult with conventional mapping techniques because the 3D geometry thereof does not accurately show depth within a space. According to one or more embodiments, one or more features hidden can be below a surface of the initial visualization. Further, the one or more features can include one or more tags (e.g., VISITAGS®), one or more catheters, one or more interior surfaces points (e.g., CARTO® points), one or more ultrasound controls, and/or one or more points. Ultrasound contours can be acquired from ultrasound catheter or other devices. From a given ultrasound FAN image several contours (continuous lines) can be drawn by the user or by an automatic algorithm, usually to mark borders of some anatomy (for example the tissue of left atria, while the ultrasound catheter is on the right atria). These contours are in 3D space and each contour is on the plane of the FAN it was extracted from. The contours are added as anatomical information to the CARTO map, similar to other data like CARTO points. Usually these contours reflect borders of anatomy, so it is expected also that the map surface passes through these contours. According to one or more embodiments, the mapping engine 101 generates the initial visualization on the display with the catheter 14 being shown at an average position as a silhouette below a surface within the initial visualization.

Figure 6:
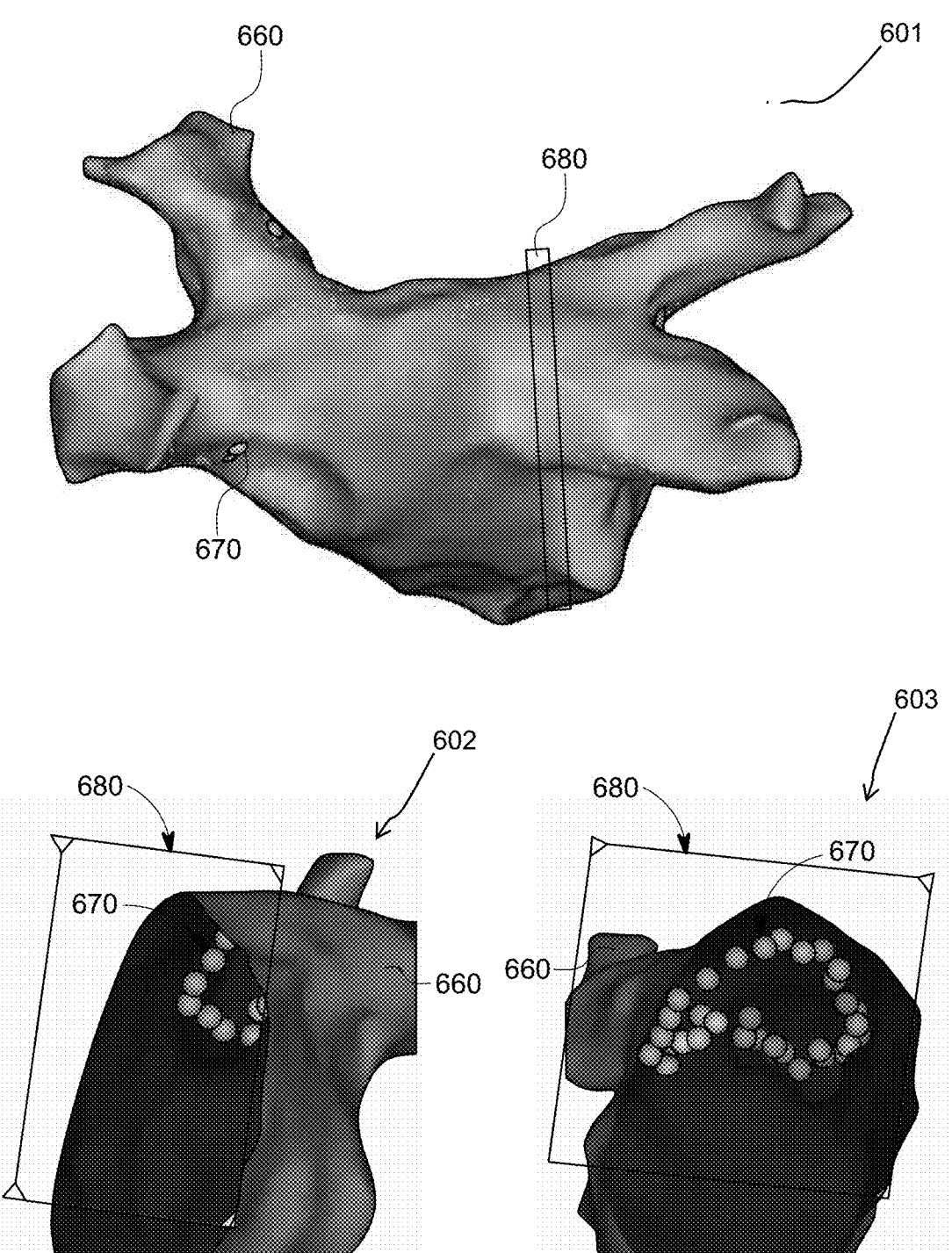
FIG. 6 depicts visualizations according to one or more embodiments.

FIG. 6 depicts visualizations 601, 602, and 603 of a surface 660 of an anatomical structure according to one or more embodiments. Each visualization 601, 602, and 603 is an example of the initial visualization generated and displayed by the mapping engine 101.

The visualization 601 can be an example of an initial visualization as generated and displayed without exposed results, points, and/or tags. In this regard, the term 'initial' of initial visualization indicates that a 3D rendering of the heart chamber that is before the EP procedure includes all previous results, points, and/or tags (e.g., the previous one or more tags 670). For instance, one or more tags 670 are below the surface 660. The one or more tags 670 being below the surface 660 is further illustrated in visualizations 602 and 603, which are cross sectional views into demarcation 680 showing the interior of the anatomical structure (i.e., below the surface 660). According to one or more embodiments, the one or more tags 670 can identify one or more previous ablation events from previous ablation procedures.

At block 530, the mapping engine 101 identifies one or more hidden features; for example features that are below a surface of the initial visualization. As noted herein, the features can include, but are not limited to, one or more tags, one or more catheters (e.g., the catheter 14), one or more interior surfaces points, and/or one or more points, as well as previous results. According to one or more embodiments, the mapping engine 101 identifies the one or more features according to a set of parameters. Examples of the set of parameters include, but are not limited to, a maximal distance, a maximal length ratio, a minimal split length, a filtering distance, or a maximal edge length, as well as a selection of the one or more tags, the one or more catheters, and/or the one or more points.

Figure 7:
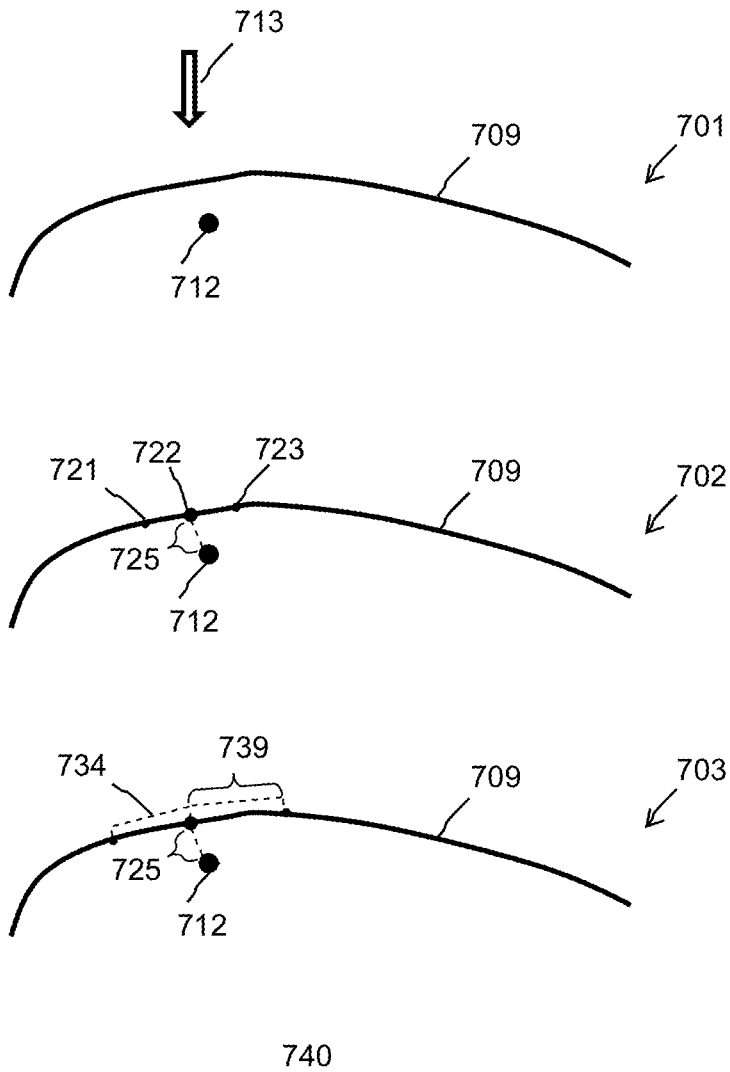
FIG. 7 depicts a set of illustrations providing an example deformation progression according to one or more embodiments.

By way of another example, turning to FIG. 7, a set of illustrations 701, 702, 703, and 704 providing an example deformation progression is shown according to one or more embodiments. Each illustration 701, 702, 703, and 704 maintains the same identifier for the same elements. As seen in the first illustration 701 of FIG. 7 and with reference to the block 530, the mapping engine 101 identifies that a surface 709 hides a feature 712 (e.g., a tag) from an external view point (represented by arrow 713) according to one or more embodiments. Further, the mapping engine 101 identifies the feature 712 as a feature to expose to the external view point. Note that the second illustration 702, the third illustration 703, and the forth illustration 704 are described in further detail herein with respect to the progression of the method 500 of FIG. 5.

By way of another example, turning to FIG. 8, a set of illustrations 801, 802, 803, and 804 providing an example deformation progression is shown according to one or more embodiments. Each illustration 801, 802, 803, and 804 maintains the same identifier for the same elements. As seen in the first illustration 801 of FIG. 8 and with reference to the block 530, the mapping engine 101 identifies that a surface 809 hides a set of features 812, 813, and 814 (e.g., tags) from an external view point (represented by arrow 815) according to one or more embodiments. Further, the mapping engine 101 identifies the one or more of the features 812, 813, and 814 as features to expose to the external view point (for example, based on the set of parameters). Note that the second illustration 802, the third illustration 803, and the forth illustration 804 are described in further detail herein with respect to the progression of the method 500 of FIG. 5.

At block 540, the mapping engine 101 deforms the initial visualization. Deforming the initial visualization can include changing a surface, a shape, or otherwise manipulating a portion of the initial visualization. The deforming of the initial visualization can be an automatic editing of the initial visualization, for example in real time during the EP procedure (e.g., an ablation procedure), and a resulting image can be considered a temporarily altered visualization (i.e., a temporary visualization). Further, 'in real time' can be considered presenting the temporary visualization upon generation on the display, such that the change to a 'present display' would only appear to the physician 24 at an area of deformation.

According to one or more embodiments, deforming the initial visualization can alter a 3D image or model (e.g., including the surface) to expose aspects (e.g., one or more features) that are otherwise hidden or covered by other portions the 3D image or model. Deformation by the mapping engine 101 is a natural change in geometry of the 3D image or model. By way of example, the mapping engine 101 changes one or more areas of the surface of the initial visualization corresponding to the one or more features or a subset thereof identified in block 530. In this regard, the mapping engine 101 lowers the surface of the 3D image or model by depressing or pitting the one or more areas towards the one or more features (e.g., an area of a surface is being reduced to a VISITAGS® and therefor expose the VISITAGS®).

The mapping engine 101 utilizes one or more algorithms to perform the deformation. According to one or more embodiments, the one or more algorithms locally deforms the initial visualization. Local deformation includes changing the shape of the 3D image or model in an area relative to a feature, for example the ablation tip of the catheter 14, while the remaining portions of the 3D image or model remain unchanged. For example, a catheter within an initial visualization may be covered by an exterior wall of the initial visualization and require adjustment to the visualization, for example by implementing a deformation that removes portions of the exterior wall to show the catheter in relation to an interior wall of the initial visualization. The local deformation enables the display of the catheter despite a presence of tags of the initial visualization. An example of the one or more algorithms includes a deformation algorithm.

According to one or more embodiments, deforming the initial visualization can be performed by the deformation algorithm of the mapping engine 101. The deformation algorithm can include, but is not limited to, an as rigid as possible (ARAP) algorithm or other geometry/mesh processing. Geometry processing includes manipulating a shape in a space of arbitrary dimensions so that a topology or collection of properties of the shape does not change after smooth transformations have been applied to the shape (e.g., unlike shaving which eliminates layers of a shape and changes the topology). According to one or more embodiments, the mapping engine 101 utilizes the ARAP algorithm to guarantee smoothness and natural deformation, both of which are unavailable with conventional mapping techniques.

Figure 9:
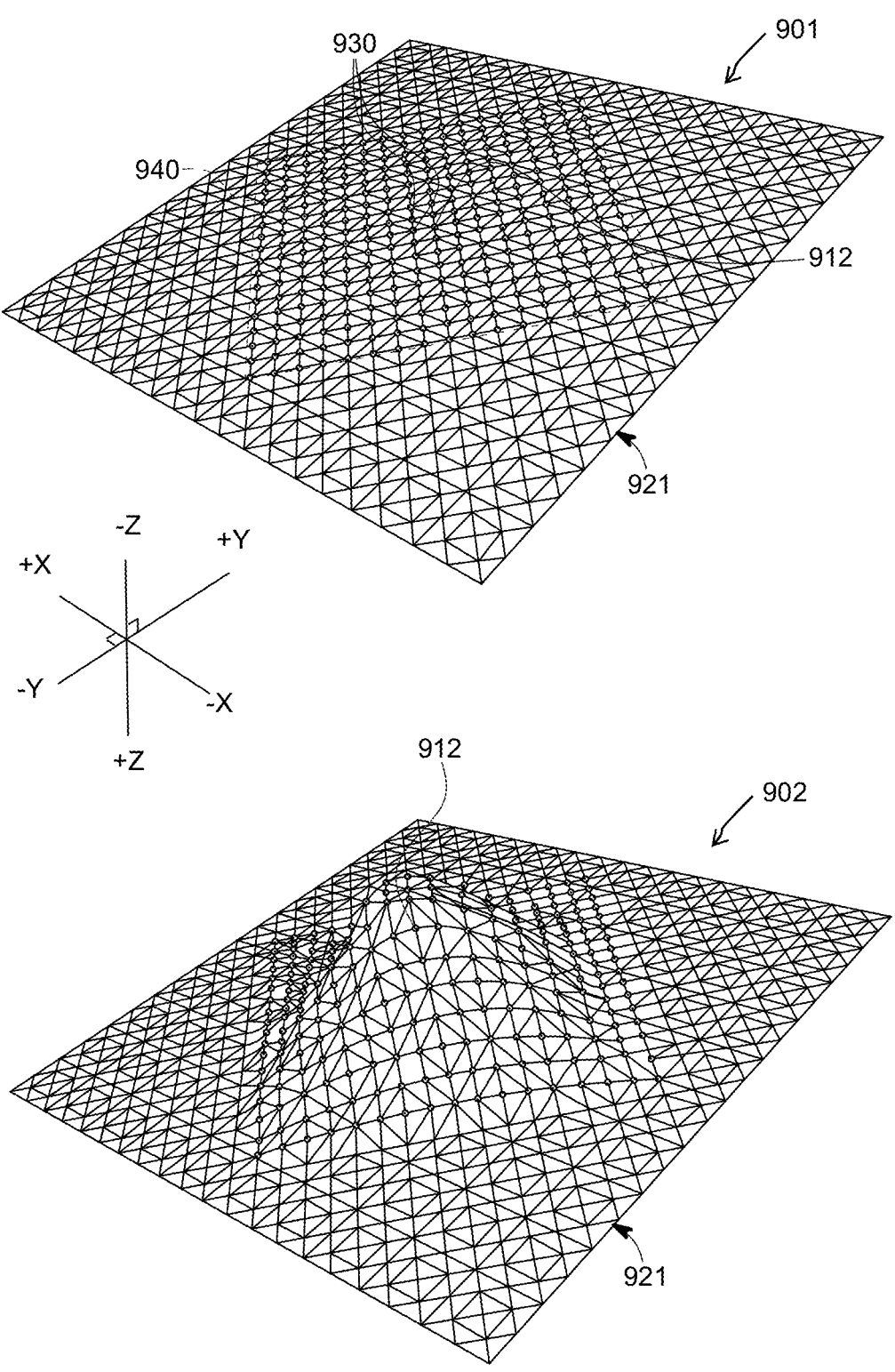
FIG. 9 depicts a set of illustrations providing an example of deformation processing according to one or more embodiments.

Note that deformation is not a shaving. Some shaving techniques require manual, time consuming work on the input of the electrical signals to the FAM in support of outputting the initial visualization. Shaving removes voxels from the acquired volume data. Shaving causes a change in the surface as it removes data that is used to build the surface. In contrast, deformation does not remove voxels (input of the surface reconstruction algorithm). Deformation occurs after the initial visualization is generated. In further contrast, deformation effects a triangular mesh of the surface of the initial visualization to contour the surface around a feature, thereby changing positions/shapes/dimensions of the triangles (e.g., vertices of each triangle within an area are change to expose the feature). By way of example, turning to FIG. 9, a set of illustrations 901 and 902 provide an example of deformation processing by the deformation algorithm of the mapping engine 101 according to one or more embodiments. The first illustration 901 shows a portion of a triangular mesh of a surface. In this regard, the triangular mesh includes a plurality of vertices on an X-Y plane 921, for example a vertex 912. As the vertex 912 is identified by the mapping engine 101, a set of immediate eight (8) neighbor vertices 930 and a region 940 of surrounding vertices are identified. The second illustration 902 shows an example deformation of the X-Y plane 921 in a-Z direction. For example, the mapping engine 101 moves the vertex 912 by pulling the vertex 912 and the immediate eight (8) neighbor vertices 930 away from the X-Y plane 921 in a-Z direction. According to one or more embodiments, the mapping engine 101 can move the vertex 912 to a tag or a feature that is separate from the X-Y plane 921 in a-Z direction. Further, the region 940 of surrounding vertices and related triangles are moved (or stretched) or changed to create a pit or a crater in the X-Y plane 921 observed from the +Z direction. According to one or more embodiments, the deformation algorithm of the mapping engine 101 can also extend the deformation constraints to local one-ring neighborhoods, allowing individual transformation for a whole ring, and prevent shearing as rings overlap.

Referring back to FIG. 5, block 540 includes two example operation sets for deforming the initial visualization by the mapping engine 101 (e.g., generating a temporary visualization on the display based on the deforming of the area). The deforming of the initial visualization can include applying a deformation algorithm to the area of the surface. The deforming of the surface is performed by the deformation algorithm according to a selection of one or more settings as described herein (a points region factor, a minimal distance, a maximal distance, a smoothing iteration value, a maximal iteration value, and/or a convergence threshold).

According to one or more embodiments, a first example operation set 541 of block 540 is shown. The first example operation set 541 includes deforming an area of the surface of the initial visualization to an average position of the catheter to generate a temporary visualization exposing at least a portion of the catheter. At sub-block 542, the mapping engine 101 determines an average position of the catheter. The average position can be a calculation of a last three positions of the catheter. Accordingly, the mapping engine 101 can maintain in a memory a history of positions of the catheter as the catheter moves. At sub-block 544, the mapping engine 101 automatically selects a surface point closest to the average position. The selection of the surface point enables the mapping engine 101 to "pull" the closest vertices to the average position of the catheter or a center of a tip of the catheter. The surface point can be a vertex of a triangle of a triangle mesh. At sub-block 546, the mapping engine 101 determining a distance between the surface point and the average position. The distance can be measured in millimeters (mm). At sub-block 548, the mapping engine 101 determines the area of the surface to deform based on the distance. The area can be a linear factor (e.g., 2×, 3×, 4×, or greater) to the distance. The linear factor can be configurable. For instance, if the distance is five (5) mm and the linear factor is 3×, the mapping engine 101 multiplies the distance by the linear factor to calculate a 15 mm radius. The area is then determined as a circle with a 15 mm radius and a center at the selected surface point from sub-block 544. According to one or more embodiments, a catheter with multiple electrodes can correspond to an effected area of the surface that is computed for each center of each electrode.

According to one or more embodiments, a second example operation set 551 of block 540 is shown. The second example operation set 551 includes deforming, by a deformation algorithm of the mapping engine 101, the surface of the initial visualization to expose a subset of the one or more features by changing one or more areas of the surface corresponding to the subset of the one or more features (e.g., tags). At sub-block 552, the mapping engine 101 automatically determines a surface point closest to a tag (for each of the one or more tags). The selection of the surface point enables the mapping engine 101 to pull the closest vertices to the tag or a center of the tag.

Referring back to FIG. 7 and as shown in the second illustration 702, a set of surface points 721, 722, and 723 (e.g., vertices of a mesh of the surface 709) are identified on the surface 709. Further, the mapping engine 101 selects a closest surface point to the feature 712 (in this example, the surface point 722 is selected).

Referring back to FIG. 8 and as shown in the second illustration 802, a set of surface points 822, 823, and 824 (e.g., vertices of a mesh of the surface 809) are identified on the surface 809. Further, the mapping engine 101 selects the closest surface point for each features 812, 813, and 814 (which are the surface points 822, 823, and 824, respectively).

Referring back to the second example operation set 551 of FIG. 5 and a next sub-block 554, the mapping engine 101 calculates a distance between one or more surface points and one or more tags.

Referring back to FIG. 7 and as shown in the second illustration 702, a distance 725 is determined by the mapping engine 101 between the surface point 722 and the feature 712.

Referring back to FIG. 8 and as shown in illustration 802, distances 833, 835, and 837 are determined by the mapping engine 101 between the surface points 822, 823, and 824 and the features 812, 813, and 814, respectively.

Referring back to the second example operation set 551 of FIG. 5 and a next sub-block 556, the mapping engine 101 determines the area of the surface to deform based on the distance.

Referring back to FIG. 7 and as shown in the third illustration 703, an area 734 is determined. For example, the area 734 can be a circle with a radius of a distance 739, and a center of the circle being contemporaneous with the surface point 722. For example, the area 734 can be a square with a half of a length of a side equating to the distance 739, and a center of the square being contemporaneous with the surface point 722. The distance 739 can be determined by the mapping engine 101. According to one or more embodiments, the distance 739 can be determined by multiplying the distance 725 by a configurable linear factor. Examples of the configurable linear factor include any number between a range of zero (0) to hundred (100) (e.g., the configurable linear factor can be 3). As shown in the fourth illustration 704, the mapping engine 101 pulls the surface 709 to the feature 712 so that the feature 712 is exposed. For example, the mapping engine 101 performs a geometric processing to move all vertices and stretch all triangles in within the area 734 to create a pit or crater 740 that exposes the feature 712.

Referring back to FIG. 8 and as shown in the second and third illustrations 802 and 803, an area 833 is determined from a distance 834, an area 835 is determined from a distance 836, and an area 837 is determined from a distance 838. Note that the areas 833, 835, and 837 can be any shape and can be determined using a configurable linear factor with respect to the distances 834, 836, and 838. As shown in the fourth illustration 804, the mapping engine 101 pulls the surface 809 to each of the features 812, 813, and 814 so that the features 812, 813, and 814 are exposed. For example, the mapping engine 101 performs a geometric processing to move all vertices and stretch all triangles in within the areas 833, 835, and 837 to create a pit or crater 841 and a channel 843 (which is due to the areas 835 and 837 overlapping) that expose the features 812, 813, and 814.

According to one or more embodiments, the mapping engine 101 makes a minimum deformation by using a convergence. The convergence is a minimizing energy function to keep a distortion of the surface minimal. The mapping engine 101 optimizes the minimum deformation by iteratively implementing an energy function, for example according to Equation 1 where $R_i$ is a rotation matrix and $v'_i$ is a new position:

$$\sum_{v_i \in M} \sum_{v_j \in N(v_i)} w_{ij} \left\| (v'_i - v'_j) - R_i(v_i - v_j) \right\|^2 \qquad \text{Equation 1}$$

Figure 10:
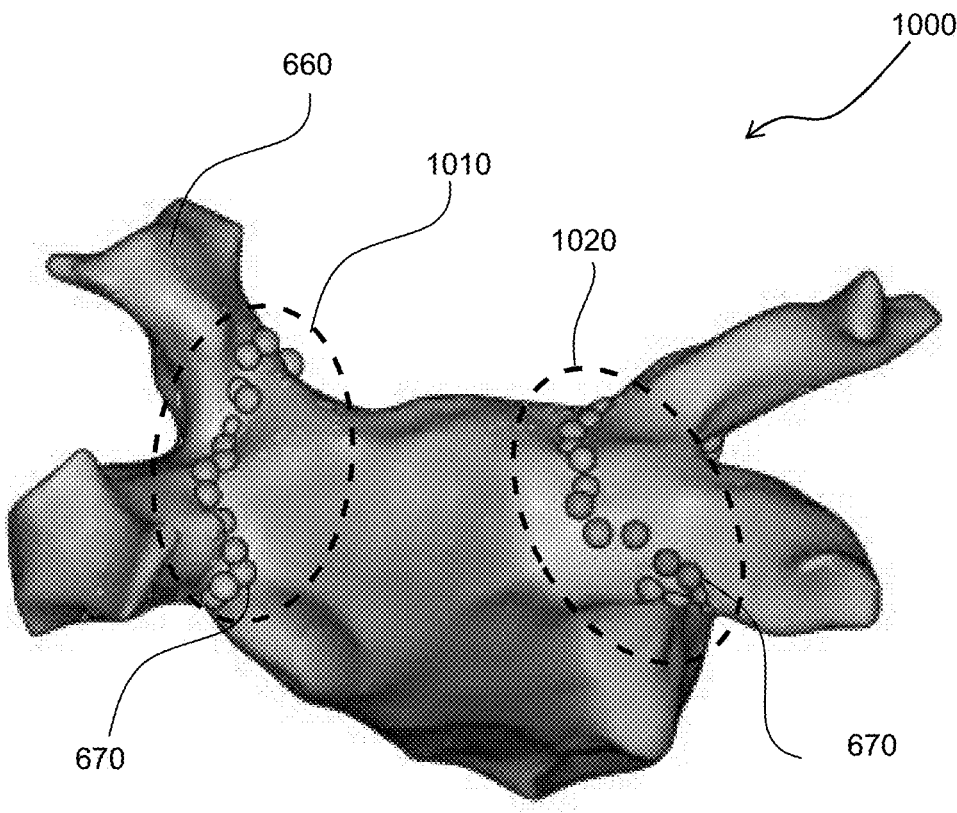
FIG. 10 depicts a visualization according to one or more embodiments.

Turning to FIG. 10, a visualization 1000 is depicted according to one or more embodiments. The visualization 1000 is a result of the deformation by the mapping engine 101. The visualization 1000 can be the temporary visualization. The visualization 1000 shows a progression from the anatomical structure shown in FIG. 6. Accordingly, the visualization 1000 depicts an 'after' state of the anatomical structure where areas corresponding to the one or more tags 670 are deformed to create recessed areas 1010 and 1020 that expose the one or more tags 670, where prior to the deformation the tags 670 were obscured under the surface 660.

Referring back to the method 500 of FIG. 5 and a next block 560, the mapping engine 101 determines whether to maintain the temporary visualization. According to one or more embodiments, the mapping engine 101 can determine whether to maintain the temporary visualization based on an ablation event of the ablation procedure. For instance, the mapping engine 101 can discard the temporary visualization and return to the initial visualization when the mapping engine 101 determines that an ablation event has not occurred (e.g., a pit, a channel, a range, a hill, a mound, or a crater resulting from pulling the surface is returned to an original state once the catheter moves, the object can return). Alternatively, the mapping engine 101 can replace the initial visualization with the temporary visualization to generate an updated visualization when the mapping engine determines that the ablation event has occurred. The updated visualization can be saved and stored.

At block 580, the mapping engine 101 receives a selection of one or more settings. According to one or more embodiments, the mapping engine 101 receives the selection of the one or more settings and updates the initial visualization or the updated visualization.

Turning to FIG. 11, a user interface 1100 is depicted according to one or more embodiments. The user interface 1100 shows an example of map deformation settings enabled by the mapping engine 101. The one or more settings include, but are not limited to, a selector 1111 for deforming to VISITAGS®, a selector 1112 for deforming to ultrasound (ULS) contours, a selector 1113 for deforming to the ablation catheter, and selector 1114 for deforming to CARTO® points. By way of example, with respect the selectors 1111 and 1112, the map deformation settings of the user interface 1100 can include selectors for a projection method with respect to an edge path and a path closest. Further, with respect to the selectors 1111 and 1112, the map deformation settings of the user interface 1100 can include a plurality of first fields. For example, the plurality of first fields can receive numerical values in millimeters (mm). The plurality of first fields can correspond to, but are not limited to, a maximal distance to map, a maximal projections/path length ratio, a minimal projection split length, a VISITAG® filtering distance, and a VISITAG® path maximal edge length. Furthermore, with respect the selector 1113, the map deformation settings of the user interface 1100 can include a plurality of second fields. For example, the plurality of second fields can receive numerical values and/or can be selectors. The plurality of first fields can correspond to, but are not limited to, a maximal distance to map, a number of ablation positions, a sampling period in milliseconds (Ms), a force threshold, and an 'only in touch' condition. The map deformation settings of the user interface 1100 can include deformation algorithm settings 1130. The deformation algorithm settings 1130 can include a plurality of third fields. The plurality of third fields can include, but are not limited to, a points region factor, a minimal point region distance, a maximal point region distance, smoothing iterations, algorithm maximal iterations, and a convergence threshold.

Figure 12:
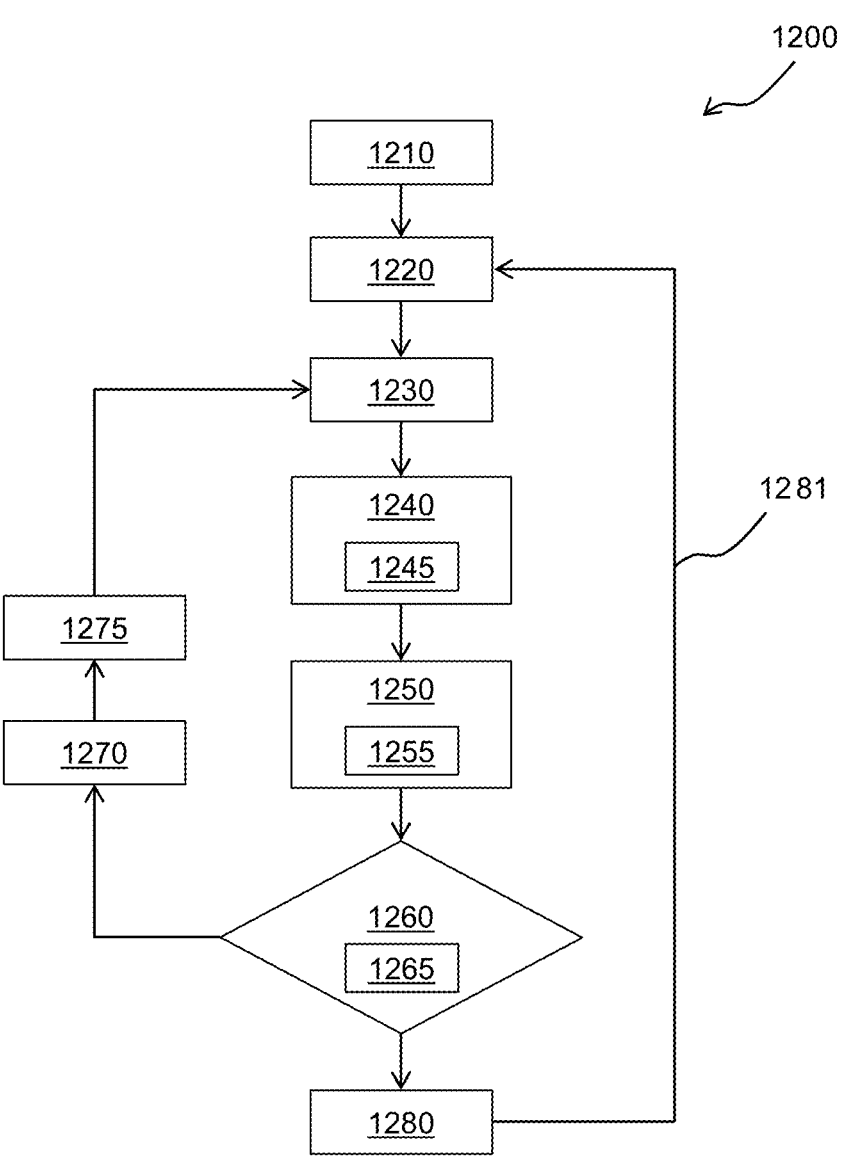
FIG. 12 depicts a method according to one or more embodiments.

Turning now to FIG. 12, a method 1200 is illustrated according to one or more exemplary embodiments. The method 1200 is an example set of operations by the mapping engine 101 being necessarily rooted in and executed by the workstation 55 of FIG. 1, the local computing device 106 of FIG. 2, the remote computing system 108 of FIG. 2, and/or the example device 400 of FIG. 4. The method 1200 shows an example of how the mapping engine 101 generates and presents maps of an anatomical structure (e.g., one or more 3D models) and edits the maps (e.g., provides map deformation one or more 3D models). FIGS. 13-23 depict user interfaces presenting a progression of visualizations according to one or more embodiments. The user interfaces of FIGS. 13-23 are provided as examples of what the physician or technician sees as the method 1200 is implemented by the mapping engine.

The method 1200 begins at block 1210, where the mapping engine 101 generates an initial visualization. The initial visualization is a map of an anatomical structure as described here. According to one or more embodiments, the initial visualization can be generated during an EP procedure. The EP procedure can be an ablation procedure, where one or more ablation events occur. At block 1220, the mapping engine 101 presents the initial visualization on a display. Accordingly, the mapping engine 101 can generate and present the initial visualization on the display during the ablation procedure. The initial visualization is used to guide the physician 24 to desired ablation sites. According to one or more embodiments, the initial visualization is generated and displayed while a catheter is moving. By way of example, the initial visualization is generated and displayed while the catheter is moving to and between ablation sites. According to one or more embodiments, the initial visualization can be provided before an ablation event of the ablation procedure so that the physician is guided to desired ablation sites with ease of understanding real tissue positioning. Referring to FIG. 13, a user interface 1300 is set forth showing an example of an initial visualization 1301 generated and displayed by the mapping engine 101. The initial visualization 1301 is a 3D rendering of a heart. The user interface 1300 includes a catheter 1320 (e.g., catheter 14 of FIG. 1), which is below a surface of the initial visualization 1301. The catheter 1320 can include an ablation tip 1330 that can change color and/or illuminate according to a state of the catheter 1320 during the ablation procedure.

Referring back to FIG. 12 and a next block 1230, the mapping engine 101 determines a catheter position. The catheter position can be an average position of the catheter 14 of FIG. 1 during the EP procedure (e.g., during an ablation event of an ablation procedure). The average position can be determined from one or more locations as provided by the catheter, as well as other biometric data. For example, the catheter can move or slide (e.g., in a slight manner) throughout the ablation event. Position and/or other information can be acquired by the mapping engine 101 as the catheter moves or slides. The position and/or other information is utilized to determine the average position as the catheter moves or slides. In this regard, the mapping engine 101 can provide a better understanding to the physician 24 as to a location of the catheter (e.g., the catheter position), rather than showing the catheter as jumping positions within the initial visualization. Additionally, body surface ECG electrodes can provide position and/or other information for determining the average position of the catheter.

According to one or more embodiments, the catheter can be any catheter as described herein, for example a focal catheter that provides force and location. According to one or more embodiments, the average position of the focal catheter may be a calculation by the mapping engine 101 based on the force and location (i.e., the position and/or other information) provided by the focal catheter over time. According to one or more embodiments, the average position can be calculated from catheter positions that meet predefined conditions, for example minimal force value, position stability, and/or touch indication. According to one or more embodiments, an ablation catheter with multiple electrodes can be used.

At block 1240, the mapping engine 101 presents the catheter within the initial visualization. For example, the mapping engine 101 displays the catheter at the average position as a silhouette or a semi-transparent silhouette in the initial visualization.

According to one or more embodiments, an ablating tip of the catheter can be displayed under a surface of an initial visualization. In this regard, the surface of the initial visualization can be semi-transparent so the ablating tip and the catheter can be shown at the determined catheter position (e.g., the mapping engine 101 displays the catheter as a semi-transparent silhouette at the catheter position). Further, as the catheter position changes due to the catheter moving deliberately, the mapping engine 101 updates the display of the catheter in accordance with the changing catheter position.

Referring back to FIG. 13, the catheter 1320 is provided within the initial visualization 1301. According to one or more embodiments, the catheter 1320 and the ablating tip 1330 of the catheter 1320 can be displayed under the endocardial surface of the initial visualization 1301. As shown, the endocardial surface can be semi-transparent (e.g., as a silhouette) so the ablating tip 1330 and the catheter 1320 can be seen on the display at the determined catheter position. Yet, the catheter 1320 is not readily understood to be at or next to the interior wall. Note that the catheter 1320 within the initial visualization 1301 is "covered" by an exterior wall of the initial visualization 1320 and requires a deformation that changes portions of the exterior wall to show the catheter 1320 in relation to an interior wall of the initial visualization 1301. Note that the mapping engine 101 can expose the catheter 1320 at any time to understand the depth within the space. Further, as the catheter position changes due to the catheter moving, the mapping engine 101 updates the user interface of the catheter 1320 in accordance with the changing catheter position.

Referring back to FIG. 12 and sub-block 1245, the mapping engine 101 enables filtering. According to one or more embodiments, the mapping engine 101 filters off catheter positions that are not relevant to a current position. For instance, movements of the catheter 1320 into a heart chamber can be filtered out of the average position determination. The mapping engine 101, thus, avoids deforming the initial visualization to a miscalculated position. Filtering can also be performed by the mapping engine 101 based on a selection of one or more factors. The one or more factors include, but are not limited to, force (e.g., no touching by the catheter with a wall of an anatomical structure, force threshold, and touch indication like a tissue touch), ablation power (e.g., power can start at high power of 5 to 10 watts), drag power (e.g., power can always be on and with varying levels), low power (e.g., ablating over, e.g., 20 seconds), and distance (e.g., a distance from the catheter itself or a distance of a surface to the catheter).

Referring to FIG. 14, a user interface 1400 is set forth showing an example of an initial visualization 1401 where an ablating tip 1410 of the catheter 1320 changes color (or is illuminated in another way). The color change indicates that the average position has been determined. Other color changes may indicate that the catheter 1320 is ready to ablate and/or that the ablation event has begun (but not concluded).

Referring back to FIG. 12 and a next block 1250, the mapping engine 101 deforms or changes a shape of the initial visualization. For example, the deformation enables the physician 24 to see the catheter despite the complexity and tags of the initial visualization. The deformation can be implemented before an ablation event, when the catheter is ready to ablate, and/or after the ablation event has begun (but prior to conclusion).

According to one or more embodiments, the mapping engine 101 deforms or changes a shape of the initial visualization using the average position. In this regard, the endocardial surface of the initial visualization is deformed to expose the catheter (i.e., the ablation tip is no longer shown as a silhouette). Deformation of the endocardial surface can be implemented by a "pull" reconstruction operation. The pull reconstruction operation includes software operations that pull/acquire biometric data, utilize the biometric data to generate a 3D geometry, and update the initial visualization with the geometry. For example, the pull reconstruction operation can include acquiring biometric data from the catheter before the ablation event. The pull reconstruction operation can be continuous while the catheter moves so that the initial visualization can be deformed to show the catheter within the 3D image or model.

According to one or more embodiments, the mapping engine 101 can utilize one or more one or more algorithms to perform the deformation. An example of the one or more algorithms includes a deformation algorithm, as described herein, to deform the initial visualization locally to the average position.

At sub-block 1255, the mapping engine 101 applies the deformation algorithm (preferably in real-time), and further deformation can occur as the catheter stabilizes (e.g., remains at a same position). The deformation algorithm can be implemented as soon as the catheter is ready to ablate and/or stable. For instance, the mapping engine 101 deforms the initial visualization at the average position to provide the temporary visualization that exposes the catheter at the average position on the display.

Referring to FIG. 15, a user interface 1500 is set forth showing an example of a temporary visualization 1501 where an ablating tip 1510 of the catheter 1320 is exposed by a deformation 1530 while a remaining portion 1540 of the catheter 1320 is shown as a silhouette. The mapping engine 101 utilizes the ARAP algorithm to guarantee smoothness of the deformation 1530 around the average position. Thus, the catheter 1320 is readily shown to be at or next to the interior wall in the temporary visualization 1501.

According to one or more embodiments, the mapping engine 101 does not wait for tags to appear during a pull reconstruction operation and/or the mapping engine 101 utilizes the average catheter position rather than preexisting tags. In this regard, the mapping algorithm is able to generate and display a temporary visualization before the ablation event occurs. Tags can take time before being displayed. However, in this example, the mapping engine

101 does not wait (proceeds immediately) for the tags (e.g., VISITAG® or ablation tags) to appear to implement the pull reconstruction operation. In contrast, conventional mapping techniques like fast anatomical mapping electro-anatomical (FAM-EA) pull the construction to the point/tag, which is too late. By way of example, a VISITAG® can annotate an ablation site objectively whenever a predefined criteria, for example catheter stability, contact force, time, impedance drop, etc., are fulfilled.

According to one or more embodiments, the locally deformed initial visualization can include a temporary visualization within the initial visualization before the ablation event concludes. Note that applying the deformation algorithm can include an automatic editing of the initial visualization in real time during the EP procedure (e.g., an ablation procedure).

Referring to FIG. 16, a user interface 1600 is set forth showing an example of a temporary visualization 1601. The temporary visualization 1601 includes the ablating tip 1510 of the catheter 1320 being further exposed. The mapping engine 101 utilizes the ARAP algorithm to enhance the temporary visualization 1601 to guarantee smoothness of a further deformation 1630. Note that the ARAP algorithm can perform one or more smoothness iterations, for example a minimum of two (2) iterations. In turn, the ablating tip 1510 of the catheter 1320 is more clearly exposed while a remaining portion 1640 of the catheter 1320 is shown as a silhouette. Note this further deformation can occur as the catheter 1320 stabilizes (e.g., as shown by an interface icon identified by arrow 1650) for at least two (2) seconds (e.g., as shown by an interface icon identified by arrow 1660). Thus, the catheter 1320 is readily shown to be at or next to the interior wall.

Referring back to FIG. 12 and a decision diamond 1260, the mapping engine 101 determines whether to maintain the temporary visualization. According to one or more embodiments, the mapping engine 101 determines whether to maintain the temporary visualization or revert to the initial visualization. According to one or more embodiments, the mapping engine 101 determines whether to maintain the temporary visualization based on an ablation event of the EP procedure. According to one or more embodiments, the mapping engine 101 can determine whether to maintain the temporary visualization based on the ablation event of the ablation procedure. That is, to determine whether to maintain the temporary visualization, the mapping engine 101 further checks (as noted by sub-block 1265) as to whether an ablation event happened. If an ablation event occurred, the process 1200 proceeds to block 1270. If an ablation event did not occur, the process 1200 proceeds to block 1280.

Figure 17:
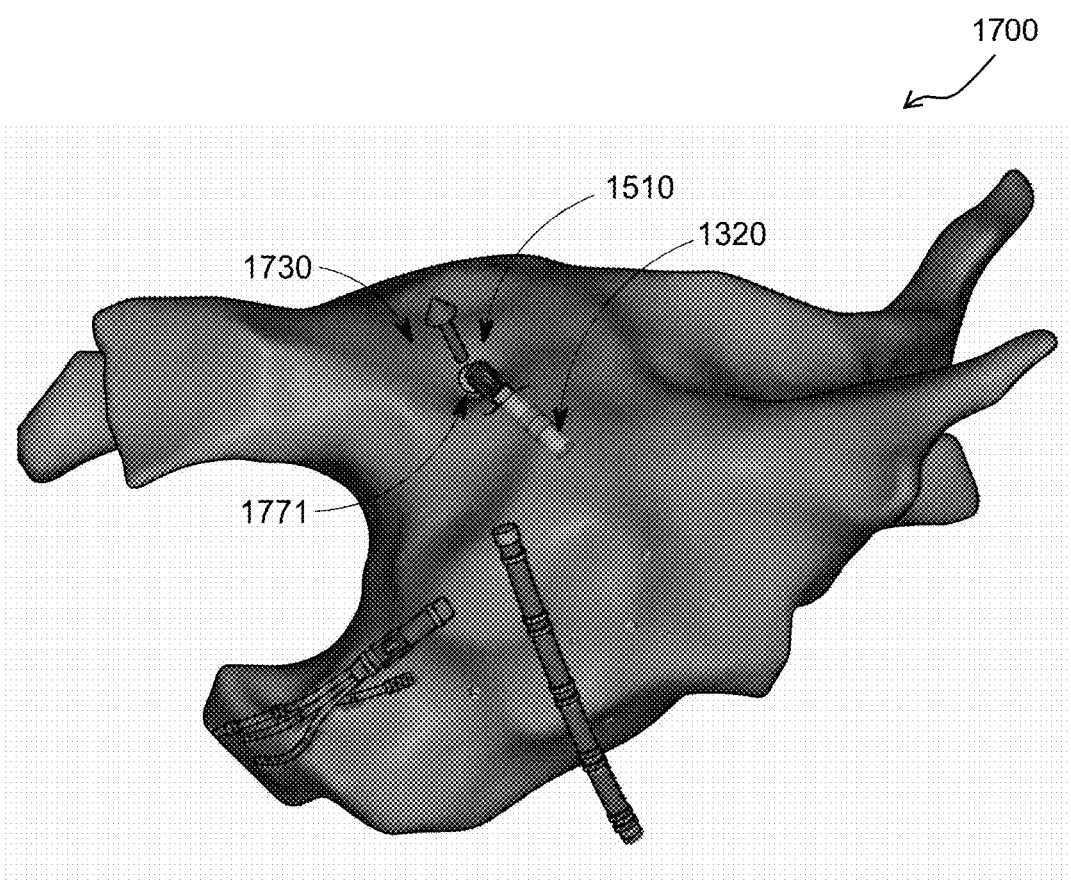

At sub-block 1265, the mapping engine 101 determines that the ablation event happened after the catheter sends a signal and/or a corresponding tag is generated. Referring to FIG. 17, a user interface 1700 is set forth showing an example of a temporary visualization 1701. The temporary visualization 1701 includes the ablating tip 1510, the catheter 1320, a deformation 1730, and a tag 1771 (represented as a sphere). The tag 1771 represents that an ablation has been performed by the catheter 1320 (e.g., an ablation event has completed). Since the ablation event occurred (as indicated by the tag 1771), the process 1200 proceeds to block 1270.

At block 1270, because an ablation event occurred, the mapping engine 101 utilizes the tag 1771 for the ablation to finalize the deformation 1730. According to one or more embodiments, the mapping engine 101 utilizes a position of a tag to apply the deformation algorithm locally when the mapping engine 101 determines that the ablation event is concluded by a detection of the tag. For example, if the ablation event is concluded with a VISITAG®, a final position of a VISITAG® is used to deform the map to the a VISITAG® position. In this regard, the mapping engine 101 presents a deformation of the initial visualization as the temporary visualization (e.g., that can be saved and stored by the mapping engine 101).

At block 1275, the mapping engine 101 replaces the initial visualization 1701 with the updated visualization 1801 so that further deformations can be made to the updated visualization 1801. Referring to FIG. 18, a user interface 1800 is set forth showing an example of an updated visualization 1801. Accordingly, a position of the tag 1771 representing the ablation event is used by the mapping engine 101 to apply deformation to the temporary visualization 1701 to generate the updated visualization 1801. In the updated visualization 1801, the catheter 1320 is shown as a silhouette and has moved from the position of the tag 1771.

According to one or more embodiments, the initial visualization 1301 and 1401, the temporary visualization 1701, and the updated visualization 1801 can be saved and stored by the mapping engine 101. According to one or more embodiments, the method 1200 loops through block 1230, block 1240, and decision diamond 1260 so that, after each ablation event, the visualization is updated with deformations and tags placed at the ablation sites. Note that while the catheter 1320 is moving, a new average position can be calculated.

Figure 19:
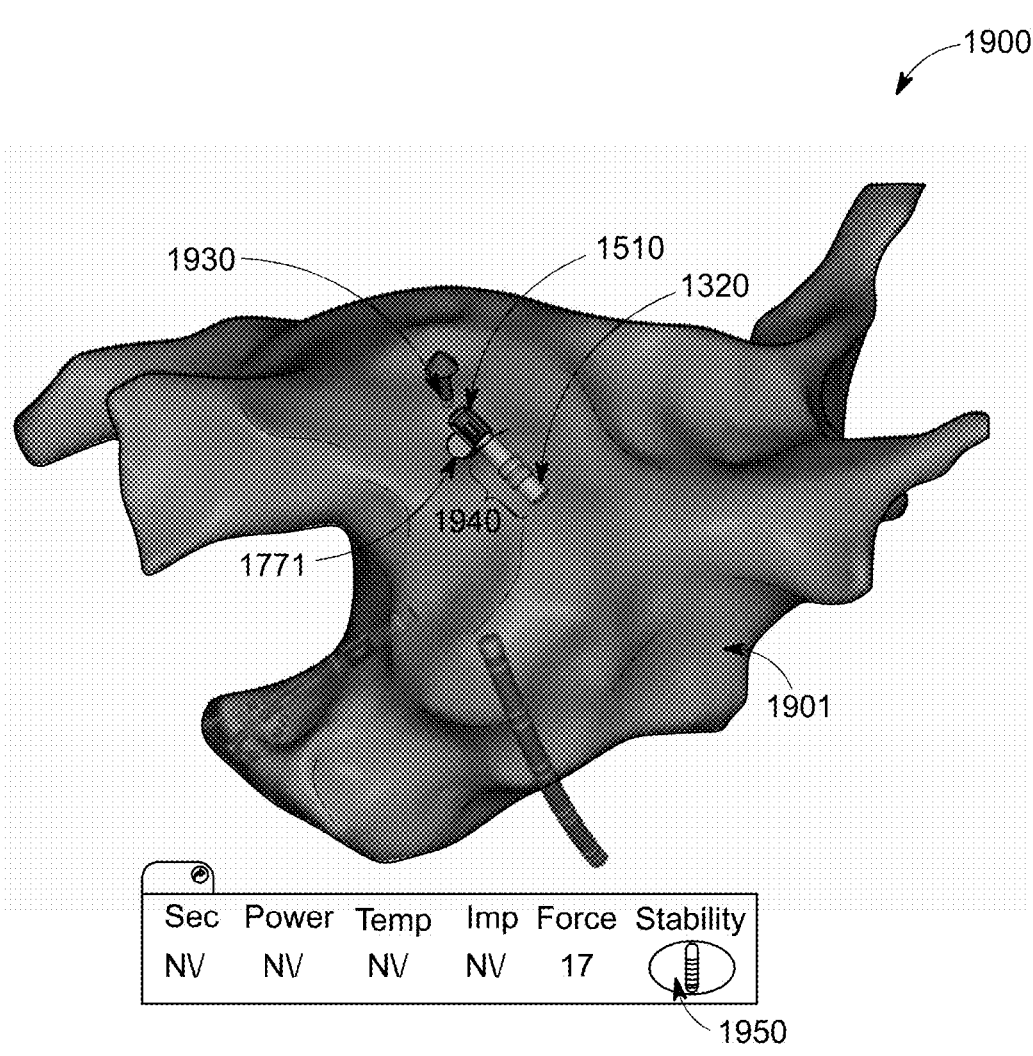
Figure 20:
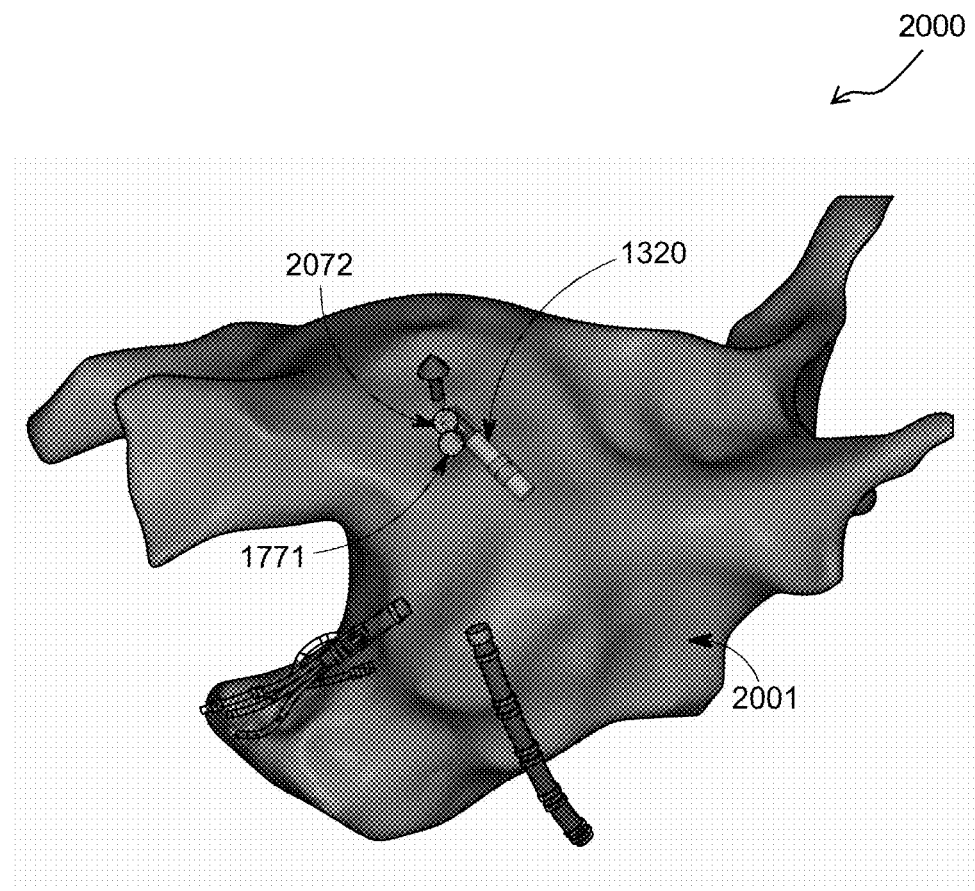
Figure 21:
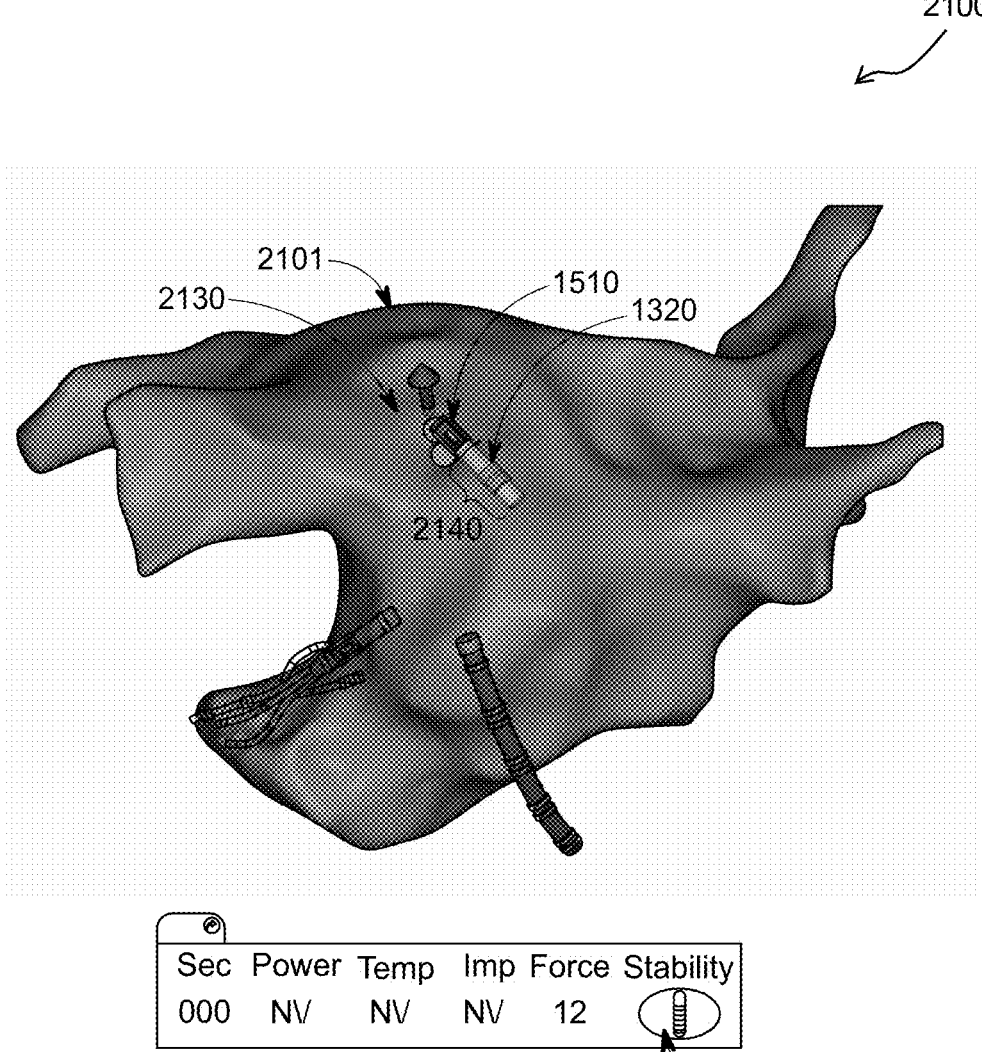
Figure 22:
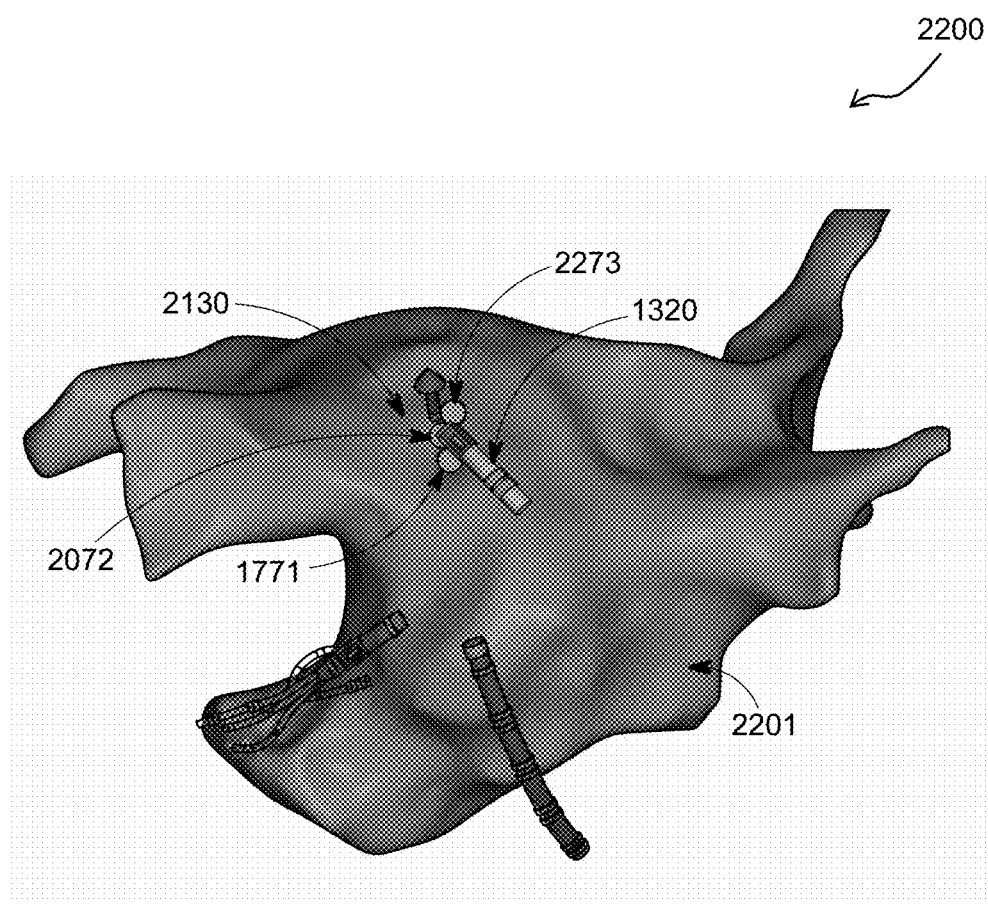

For example, referring to FIG. 19, a user interface 1900 sets forth an example of a subsequent temporary visualization 1901 where an ablating tip 1510 of the catheter 1320 is exposed by a deformation 1930 while a remaining portion 2040 of the catheter 1320 is shown as a silhouette. Note that the tag 1771 is exposed while the deformation 1930 is performed by the mapping engine 101. Further, referring to FIG. 20, a user interface 2000 sets forth an example of a subsequent temporary visualization 2001 after a second ablation event occurs. The subsequent temporary visualization 2101 includes the catheter 1320, the tag 1771, and a second tag 2072 (represented as a sphere). The tag 2072 represents that an ablation has been performed by the catheter 1320 (e.g., an ablation event has completed). Since the second ablation event occurred (as indicated by the second tag 2072), the process 1200 proceeds through blocks 1270 and 1275. Furthermore, referring to FIG. 21, a user interface 2100 sets forth an example of a subsequent temporary visualization 2101 where the ablating tip 1510 of the catheter 1320 is exposed by a deformation 2130 while a remaining portion 2140 of the catheter 1320 is shown as a silhouette. Note this further deformation can occur as the catheter 1320 stabilizes (e.g., as shown by an interface icon identified by arrow 2150). Also, the ablating tip 2110 of the catheter 1320 can change color (or is illuminated in another way) to indicate that the catheter 1320 is stable and the average position of the catheter 1320 has been determined by the mapping engine 101. Additionally, referring to FIG. 22, a user interface 2200 sets forth an example of a temporary visualization 2201. The temporary visualization 2201 includes the catheter 1320, the deformation 2130, the first tag 1771, the second tag 2072, and a third tag 2273. The deformation 2130 is now set to the third tag 2273. Since the third ablation event occurred (as indicated by the third tag 2273), the process 1200 proceeds through blocks 1270 and 1275.

Referring back to FIG. 12 and returning to decision block 1260, if an ablation event did not occur, the process 1200 proceeds to block 1280. At block 1280, the mapping engine 101 reverts to the initial visualization without the deformation or one of the temporary visualizations. The temporary visualization (i.e., the deformation of the initial visualization) is discarded when the mapping engine 101 determines that the ablation event is not concluded. In this regard, the mapping engine 101 deletes or removes the deformation from the initial visualization to end a presentation of the temporary visualization. By way of further example, the mapping engine 101 deletes or removes any added deformation to revert to a 'previous' visualization. According to one or more embodiments, the initial visualization reverts the surface to a previous surface shape, at that location. Note the process 1200 can loop (as shown by arrow 1281), so that further or alternative deformations can be made.

According to one or more embodiments, the deformation of the initial visualization is discarded when the mapping engine 101 determines that the ablation event is not concluded. For example, if the ablation event is not concluded with the VISITAG®, the deformation is discarded. In this regard, the mapping engine 101 deletes or removes the deformation from the initial visualization to end a presentation of the temporary visualization.

Figure 23:
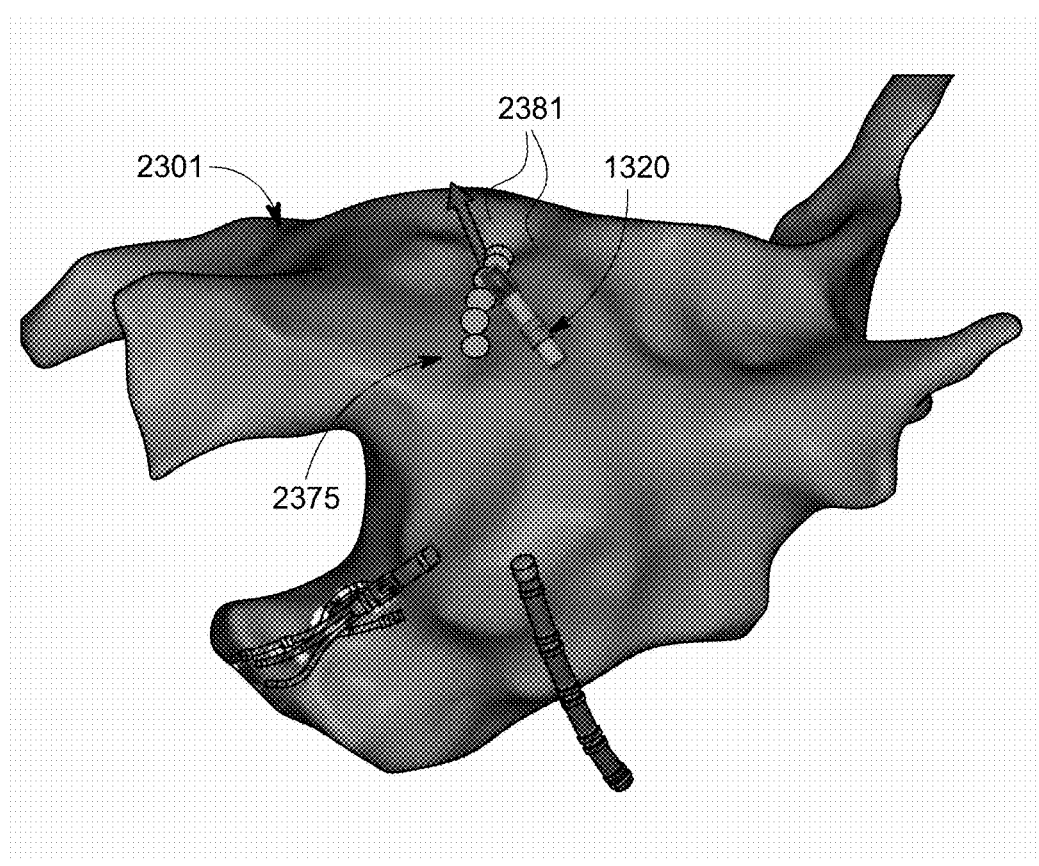

A user interface 2300 is set forth by FIG. 23 showing an example of a final visualization 2301. The final visualization 2301 includes the catheter 1320 and the plurality of tags 2375 shown by a continued deformation 2381 (e.g., a deformed area of a surface) within the final visualization 2301.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, for example radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media (e.g., internal hard disks and removable disks), magneto-optical media, optical media (e.g., compact disks (CD) and digital versatile disks (DVDs)), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for enhancing visualization of a catheter during an ablation procedure by dynamically modifying a displayed anatomical surface to expose sub-surface features, the method comprising:
   generating on a display an first visualization of an anatomical structure during the ablation procedure;
   generating on the display the catheter at an average position as a silhouette below a surface within the first visualization; and
   deforming an area of the surface of the first visualization to the average position to generate a second visualization exposing at least a portion of the catheter.

2. The method of claim 1, wherein the method further includes:
   determining the average position of the catheter and deforming the surface of the first visualization upon the determining of the average position.

3. The method of claim 1, wherein the deforming of the area of the surface of the first visualization comprises:
   automatically selecting of a surface point closest to the average position;
   determining a distance between the surface point the average position; and
   determining the area of the surface to deform based on the distance.

4. The method of claim 1, wherein the deforming of the area of the surface of the first visualization comprises applying a deformation algorithm to the area.

5. The method of claim 1, wherein the method further comprises:

discarding the second visualization and returning to the first visualization when an ablation event has not occurred within a predetermined time period.

6. The method of claim 1, wherein the method further comprises:

replacing the first visualization with the second visualization to generate an updated visualization when an ablation event has occurred within a predetermined time period.

7. A method for enhancing intraoperative visualization of anatomical tags by dynamically modifying a displayed anatomical surface in a localized manner, the method comprising:

generating on a display a visualization of an anatomical structure comprising one or more tags hidden below a surface of the visualization; and applying a deformation algorithm to deform a localized area of the surface to expose the one or more tags, wherein, for each of the one or more tags, the deformation algorithm includes:

automatically selecting a surface point closest to a tag of the one or more tags, calculating a distance between the surface point and the tags, and determining an area of the surface to deform based on the distance and one or more deformation parameters associated with the deformation algorithm.

8. The method of claim 7, wherein the area of the surface is deformed to expose the one or more tags comprises a change to the visualization to generate a temporary visualization.

9. The method of claim 7, wherein the method further comprises:

identifying the one or more tags according to a set of parameters comprising a maximal distance to map.

10. The method of claim 7, wherein the method further comprises:

identifying the one or more tags according to a set of parameters comprising filtering distance.

11. The method of claim 8, wherein the method comprises:

discarding the temporary visualization when an ablation event has not occurred within a predetermined time period.

12. The method of claim 8, wherein the method comprises:

replacing the visualization with the a visualization to generate an updated visualization when an ablation event has occurred within a predetermined time period.

13. A method for enhancing visualization of subsurface anatomical features during a medical procedure, the method comprising:

generating on a display a visualization of an anatomical structure comprising one or more features hidden below a surface of the visualization;

identifying a subset of the one or more features based on spatial proximity to the surface and according to a set of parameters defining deformation criteria; and deforming, by a deformation algorithm, a localized portion of the surface of the visualization to expose the subset of the one or more features, wherein the deforming comprises modifying surface geometry in a region surrounding each identified feature based on a computed distance between the features and the surface and based on one or more deformation control values associated with the deformation algorithm.

14. The method of claim 13, wherein the one or more features comprises one or more tags, a catheter, or one or more points.

15. The method of claim 14, wherein the set of parameters comprises at least of selection of the one or more tags, the catheter, or the one or more points.

16. The method of claim 13, wherein the set of parameters comprises a maximal distance, a maximal length ratio, a minimal split length, a filtering distance, or a maximal edge length.

17. The method of claim 13, wherein the deformation algorithm comprises an As Rigid as Possible (ARAP) algorithm.

18. The method of claim 13, wherein the deforming of the surface is performed by the deformation algorithm according to a selection of one or more settings comprising one or more of a points region factor, a minimal distance, a maximal distance, a smoothing iteration value, a maximal iteration value, and a convergence threshold.

* * * * *